(12) United States Patent
Hlavka et al.

(10) Patent No.: US 8,311,626 B2
(45) Date of Patent: Nov. 13, 2012

(54) ROBOTICALLY CONTROLLED INTRAVASCULAR TISSUE INJECTION SYSTEM

(75) Inventors: Edwin J. Hlavka, Minneapolis, MN (US); Daniel T. Wallace, Santa Cruz, CA (US); Frederic H. Moll, San Francisco, CA (US)

(73) Assignee: Hansen Medical, Inc., Mountain View, CA (US)

( * ) Notice: Subject to any disclaimer, the term of this patent is extended or adjusted under 35 U.S.C. 154(b) by 0 days.

(21) Appl. No.: 13/188,312

(22) Filed: Jul. 21, 2011

(65) Prior Publication Data

US 2012/0016291 A1 Jan. 19, 2012

Related U.S. Application Data

(63) Continuation of application No. 11/202,925, filed on Aug. 12, 2005, now Pat. No. 8,005,537.

(60) Provisional application No. 60/600,869, filed on Aug. 12, 2004, provisional application No. 60/644,505, filed on Jan. 13, 2005, provisional application No. 60/677,580, filed on May 3, 2005, provisional application No. 60/678,097, filed on May 4, 2005.

(51) Int. Cl.
*A61N 1/30* (2006.01)
(52) U.S. Cl. ........ 604/21; 604/97.02; 600/114; 600/437
(58) Field of Classification Search .......... 600/407–424, 600/437, 473–480, 101, 109, 114, 117, 118, 600/139, 146; 606/130; 604/21, 97.02, 121–124
See application file for complete search history.

(56) References Cited

U.S. PATENT DOCUMENTS

| 5,389,076 A | 2/1995 | Shaw et al. |
| 5,391,199 A | 2/1995 | Ben-Haim |
| 5,722,959 A | 3/1998 | Bierman |
| 5,845,646 A | 12/1998 | Lemelson |
| 6,004,271 A | 12/1999 | Moore |
| 6,061,587 A | 5/2000 | Kucharczyk et al. |
| 6,123,665 A | 9/2000 | Kawano et al. |
| 6,381,483 B1 | 4/2002 | Hareyama et al. |
| 6,490,468 B2 | 12/2002 | Panescu et al. |
| 6,530,913 B1 | 3/2003 | Giba et al. |
| 6,544,230 B1 | 4/2003 | Flaherty et al. |
| 6,551,273 B1 | 4/2003 | Olson et al. |

(Continued)

FOREIGN PATENT DOCUMENTS

WO WO 02/065933 8/2002

OTHER PUBLICATIONS

PCT International Search Report for PCT/US2005/028877, Applicant Hansen Medical, Inc., Forms PCT/ISA/210 and 220, dated Nov. 22, 2205 (7 pages).

(Continued)

*Primary Examiner* — Sanjay Cattungal
(74) *Attorney, Agent, or Firm* — Vista IP Law Group LLP

(57) ABSTRACT

A robotic catheter system includes a controller including a master input device and instrument driver in communication with the controller. An elongate flexible guide instrument is operatively coupled to the instrument driver. A fluid injection needle may be advanced from, or retracted into, a distal portion of the guide instrument.

10 Claims, 43 Drawing Sheets

U.S. PATENT DOCUMENTS

| | | |
|---|---|---|
| 6,610,007 B2 | 8/2003 | Belson et al. |
| 6,669,709 B1 | 12/2003 | Cohn et al. |
| 6,673,041 B1 | 1/2004 | Macoviak |
| 6,733,458 B1 | 5/2004 | Steins et al. |
| 6,769,963 B2 | 8/2004 | Mitsui et al. |
| 6,853,193 B2 | 2/2005 | Riederer et al. |
| 6,905,460 B2 | 6/2005 | Wang et al. |
| 6,911,019 B2 | 6/2005 | Mulier et al. |
| 7,214,230 B2 | 5/2007 | Brock et al. |
| 7,276,044 B2 | 10/2007 | Ferry et al. |
| 7,371,210 B2 | 5/2008 | Brock et al. |
| 7,404,824 B1 | 7/2008 | Webler et al. |
| 7,413,568 B2 | 8/2008 | Swanson et al. |
| 7,425,200 B2 | 9/2008 | Brockway et al. |
| 7,607,440 B2 | 10/2009 | Coste-Maniere et al. |
| 7,699,805 B2 | 4/2010 | Mulier et al. |
| 7,699,835 B2 | 4/2010 | Lee et al. |
| 7,766,894 B2 | 8/2010 | Weitzner et al. |
| 7,778,688 B2 | 8/2010 | Strommer |
| 7,840,252 B2 | 11/2010 | Strommer et al. |
| 7,901,348 B2 | 3/2011 | Soper et al. |
| 7,972,298 B2 | 7/2011 | Wallace et al. |
| 7,976,539 B2 * | 7/2011 | Hlavka et al. ............... 606/27 |
| 2003/0073908 A1 * | 4/2003 | Desai ............... 600/464 |
| 2003/0074011 A1 | 4/2003 | Gilboa et al. |
| 2003/0135204 A1 | 7/2003 | Lee et al. |
| 2004/0176751 A1 | 9/2004 | Weitzner et al. |
| 2005/0159789 A1 | 7/2005 | Brockway et al. |
| 2005/0182330 A1 | 8/2005 | Brockway et al. |
| 2006/0058647 A1 | 3/2006 | Strommer et al. |
| 2006/0258938 A1 | 11/2006 | Hoffman et al. |
| 2006/0271036 A1 * | 11/2006 | Garabedian et al. ............ 606/41 |
| 2007/0038181 A1 * | 2/2007 | Melamud et al. ............ 604/158 |
| 2008/0300592 A1 * | 12/2008 | Weitzner et al. ............ 606/41 |
| 2009/0054884 A1 | 2/2009 | Farley et al. |
| 2009/0182224 A1 | 7/2009 | Shmarak et al. |

OTHER PUBLICATIONS

PCT Written Opinion for PCT/US2005/028877, Applicant Hansen Medical, Inc., Form PCT/ISA/237, dated Nov. 22, 2005 (5 pages).

* cited by examiner

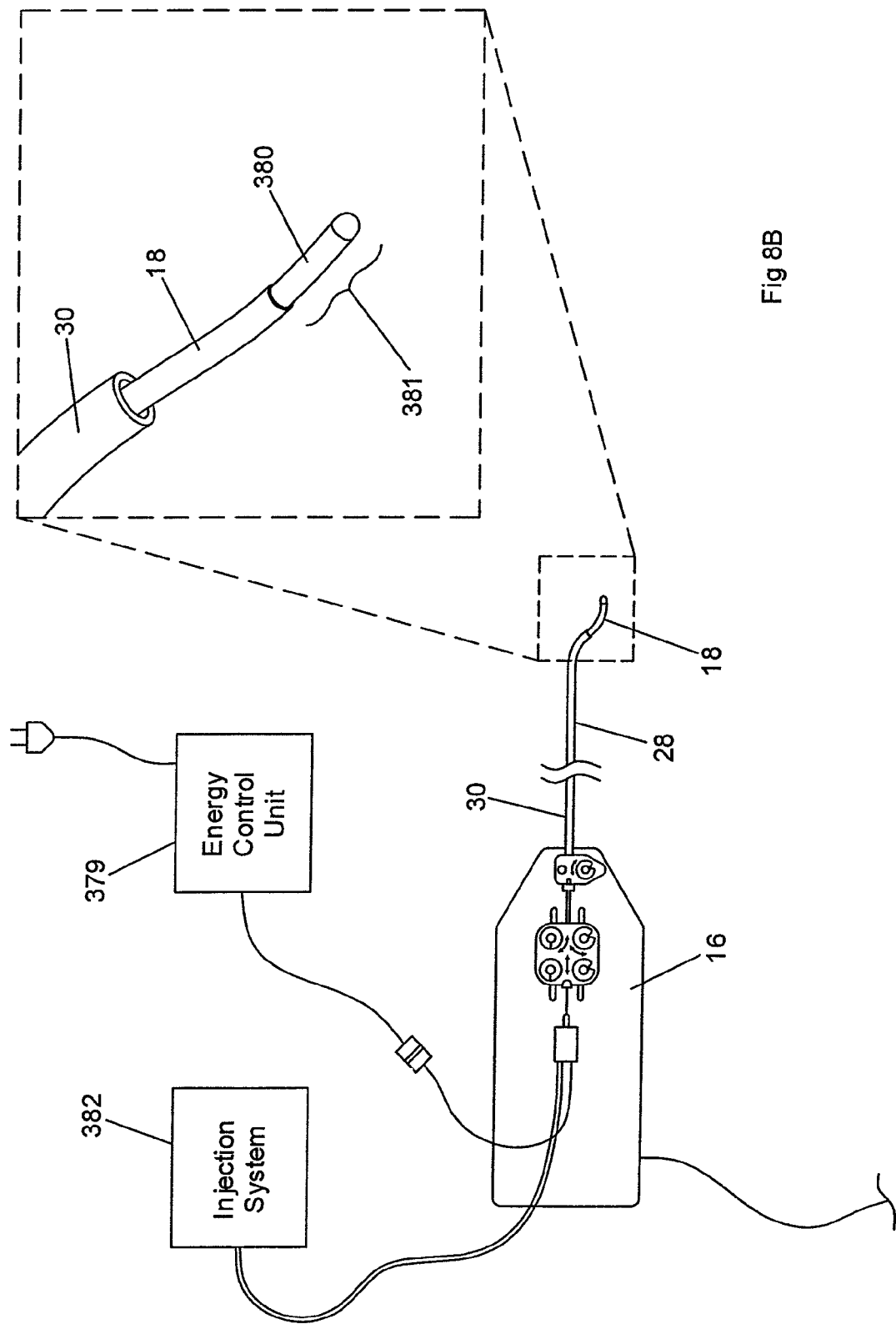

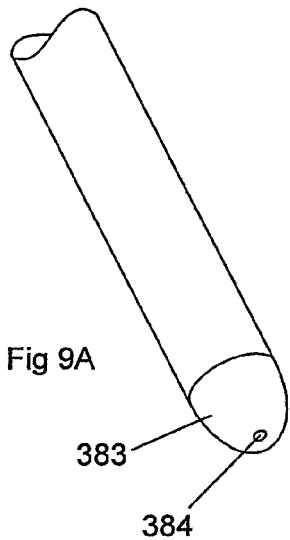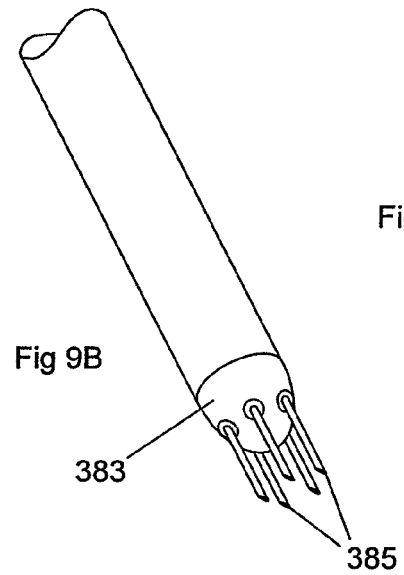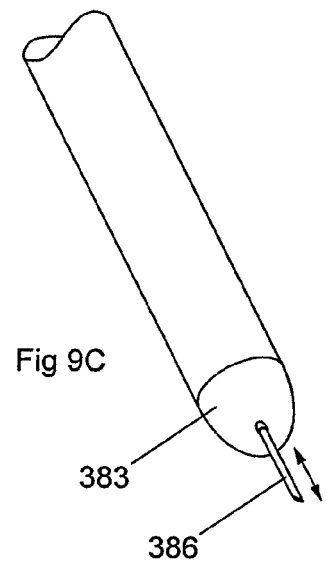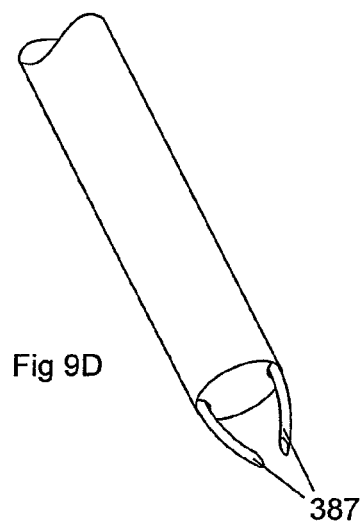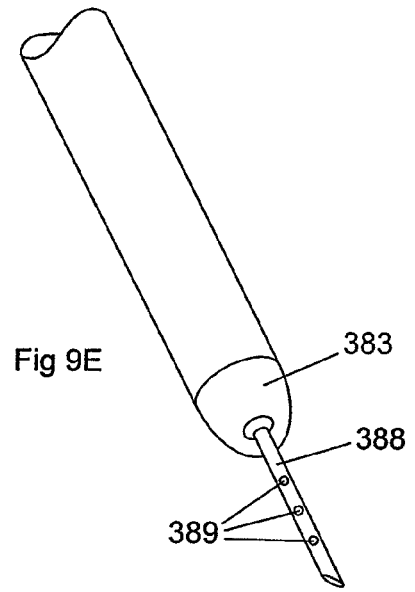

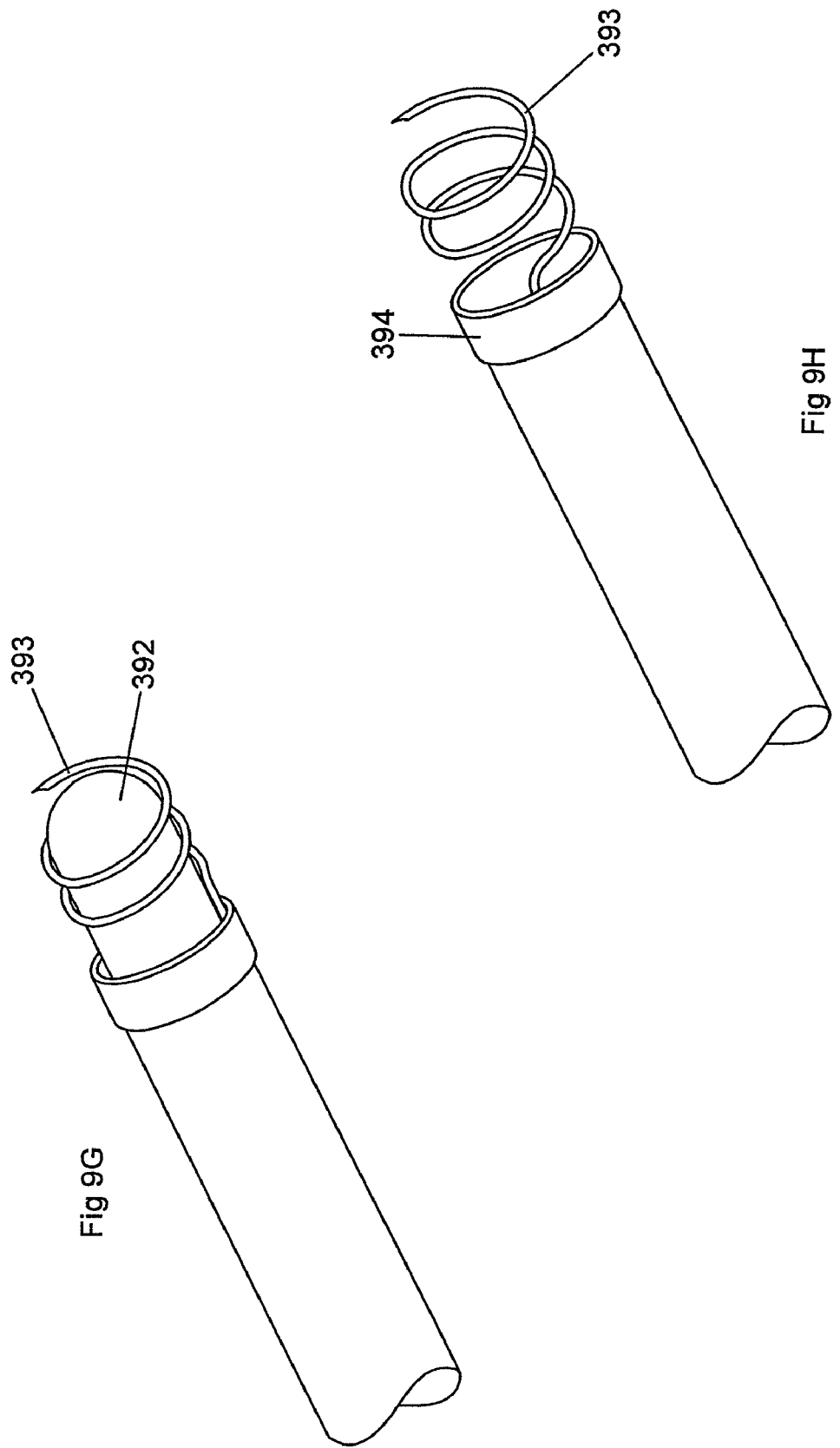

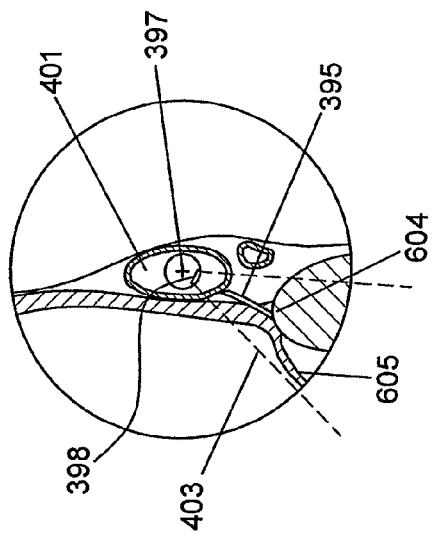
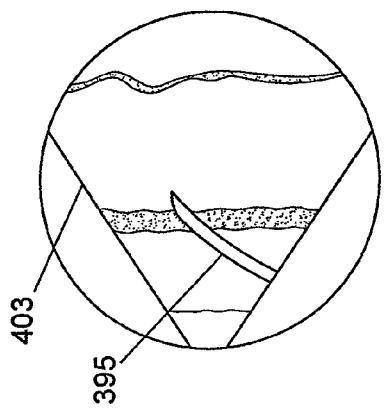
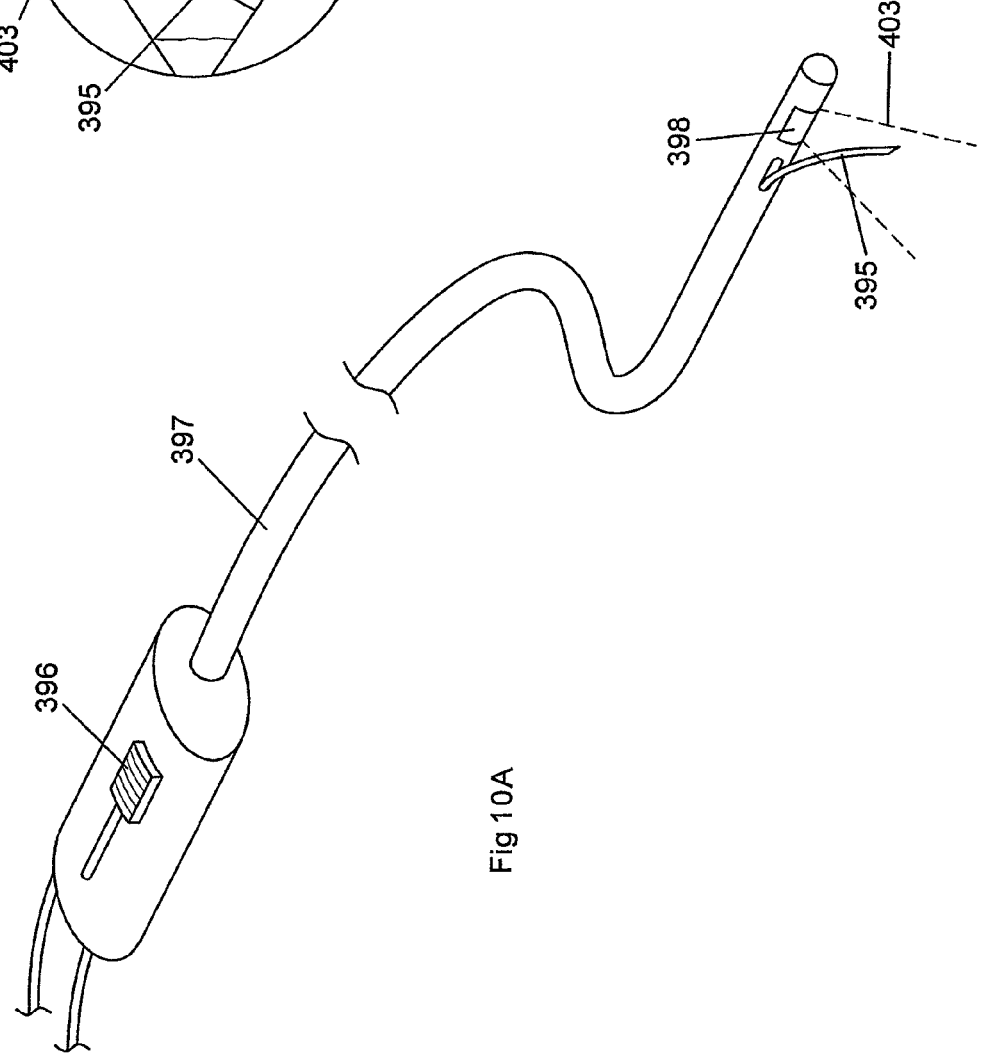

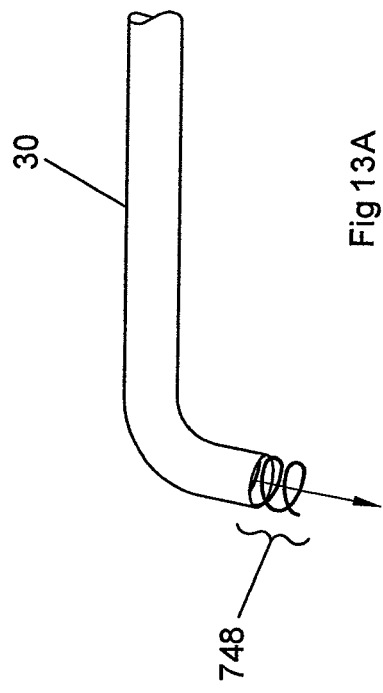
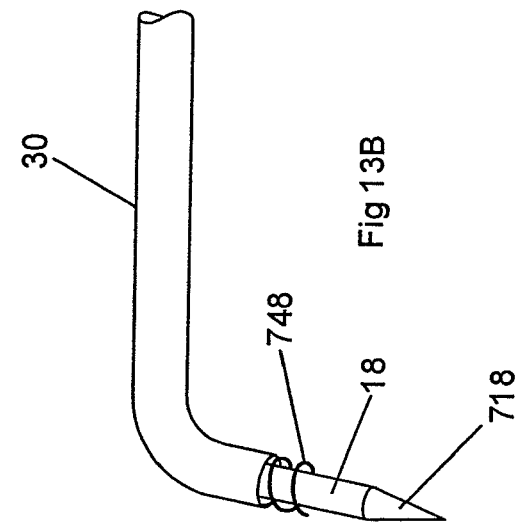
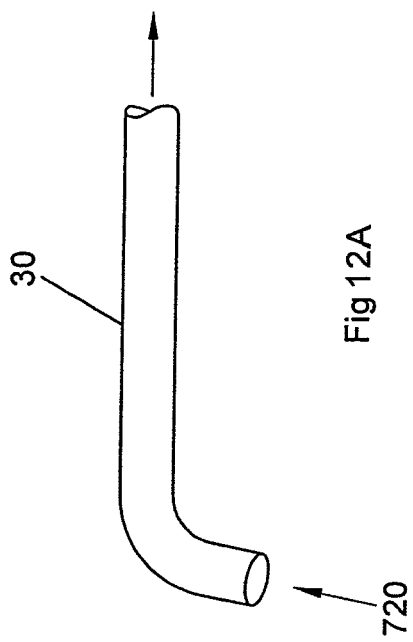
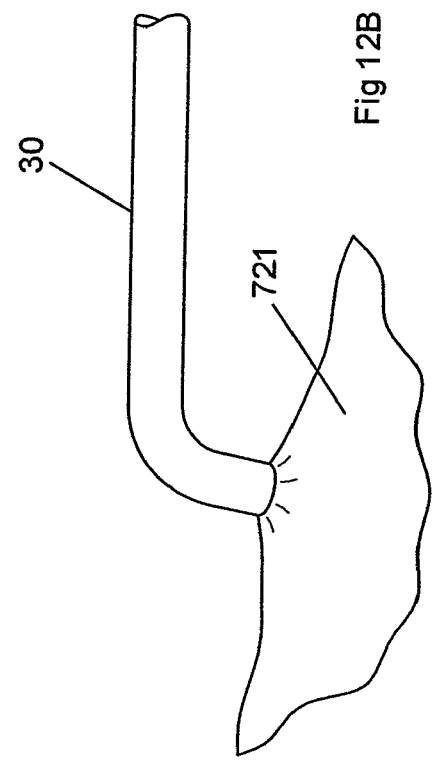

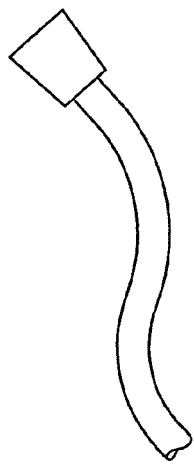
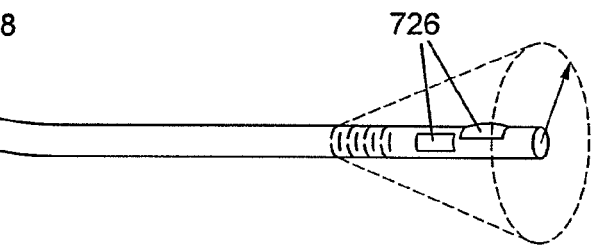
Fig 15
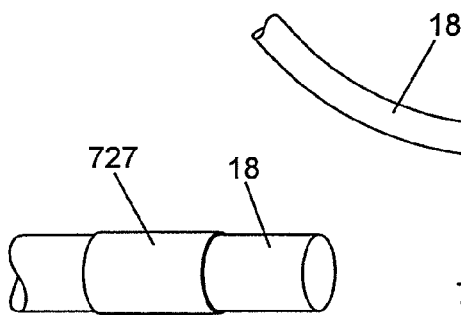
Fig 16A
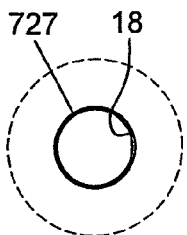
Fig 16B
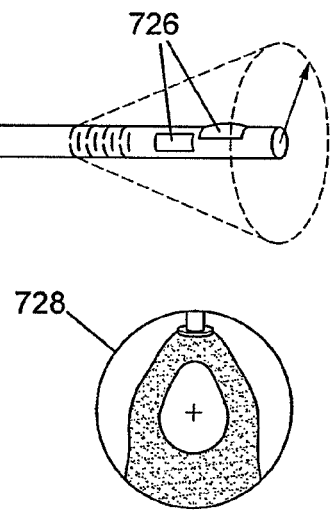
Fig 16C
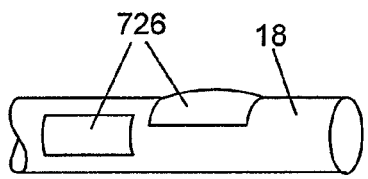
Fig 17A
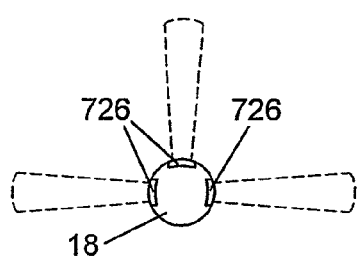
Fig 17B
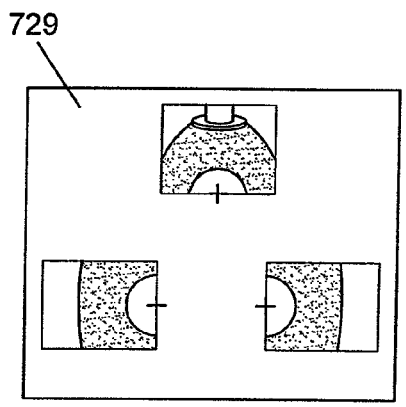
Fig 17C

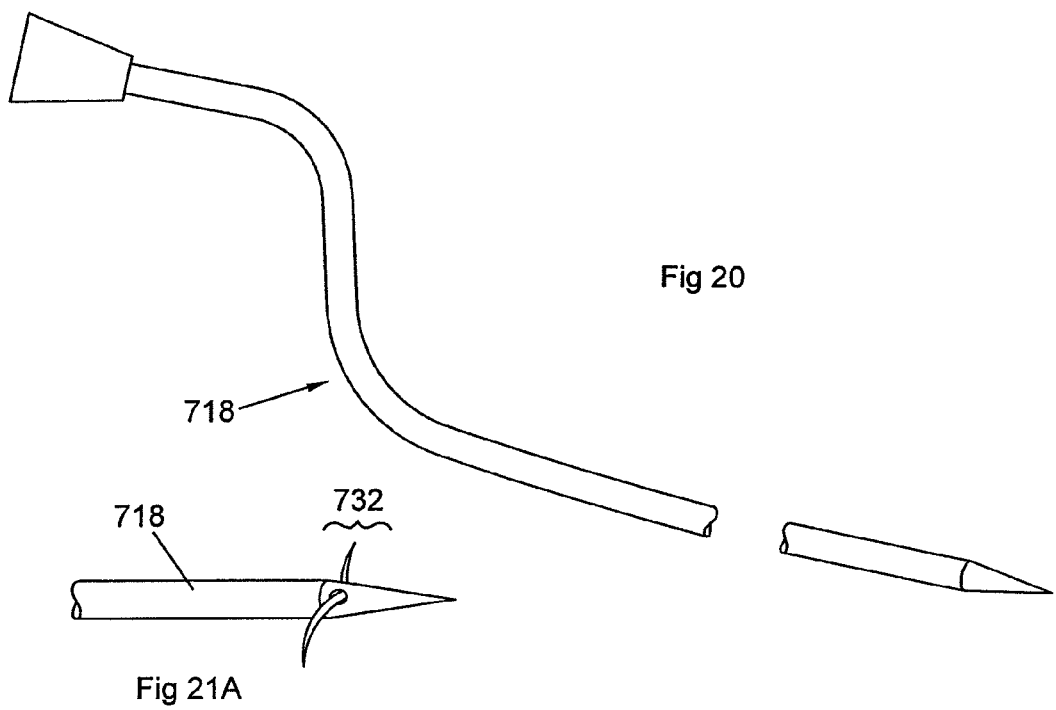
Fig 20
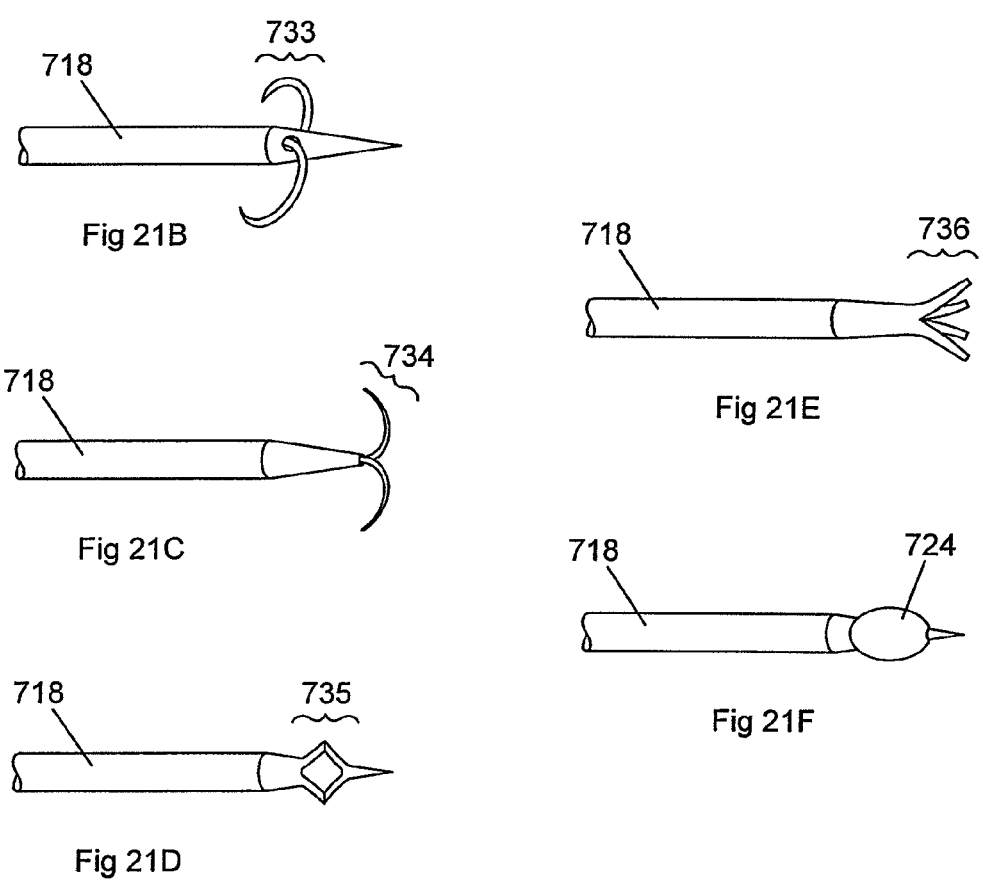
Fig 21A
Fig 21B
Fig 21C
Fig 21D
Fig 21E
Fig 21F

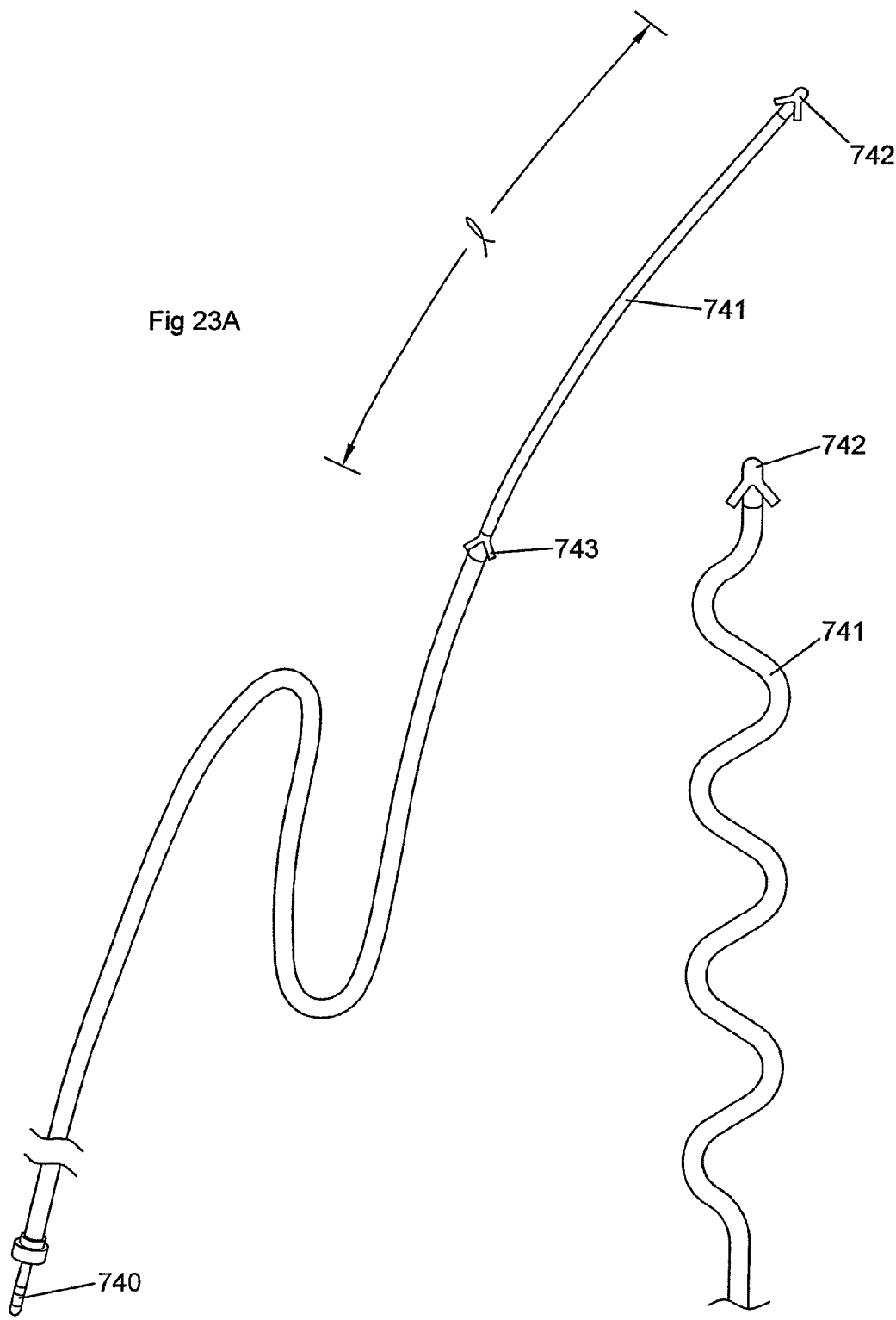

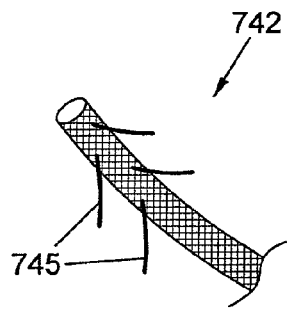
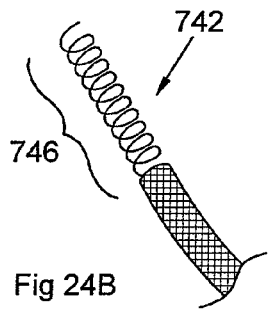
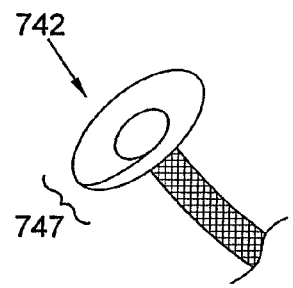
Fig 24A    Fig 24B    Fig 24C
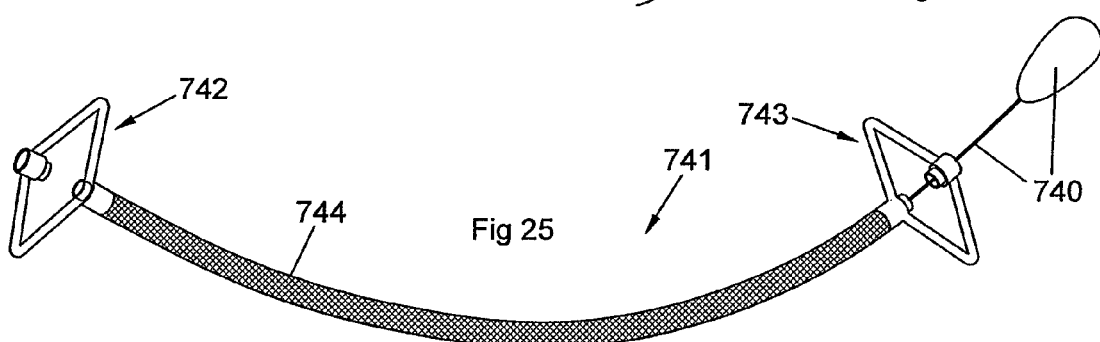
Fig 25
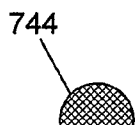
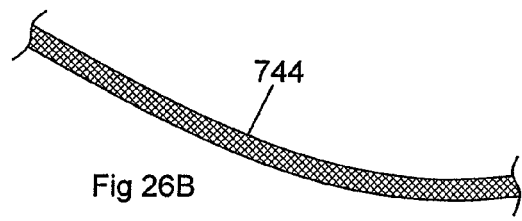
Fig 26A    Fig 26B
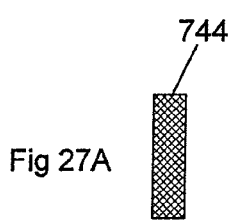
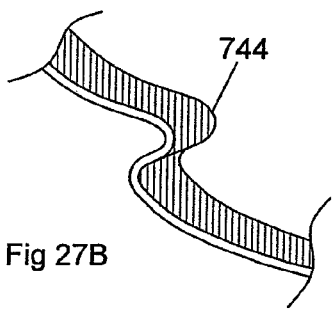
Fig 27A    Fig 27B
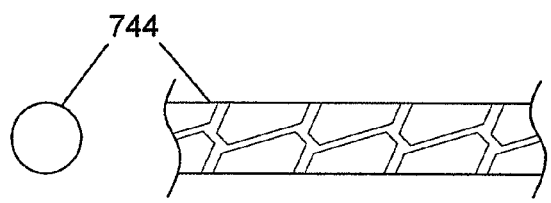
Fig 28A
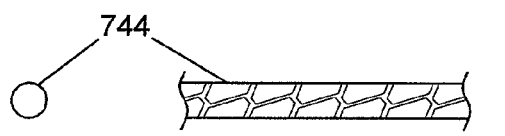
Fig 28B

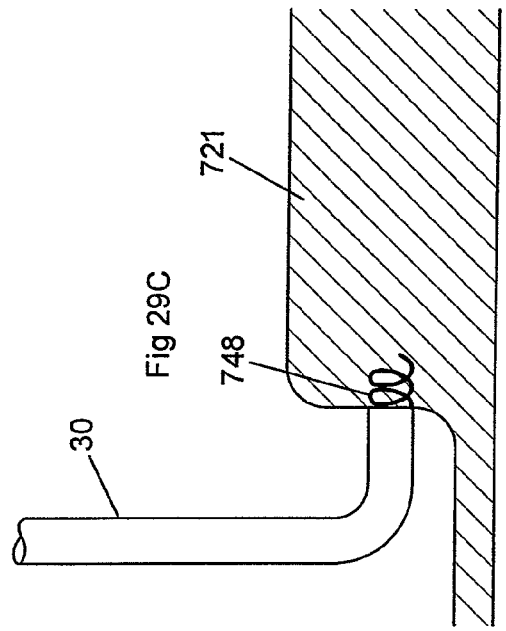
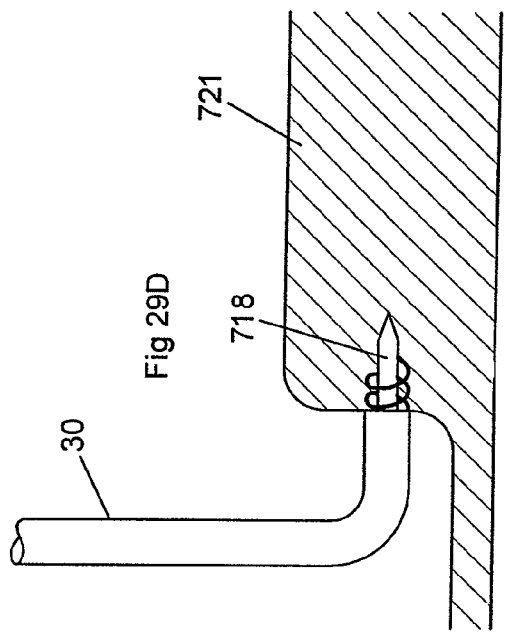
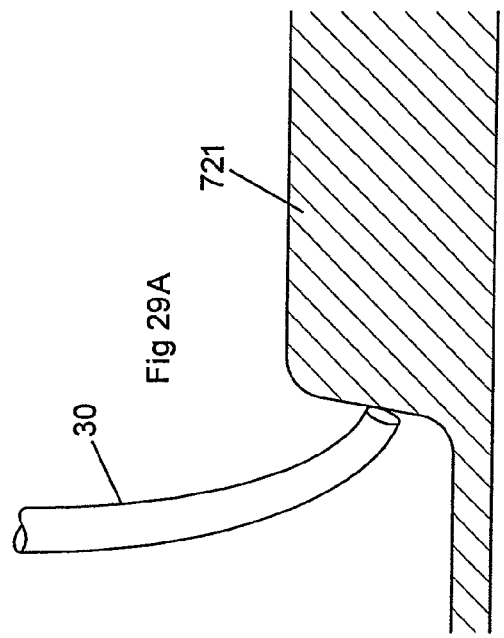
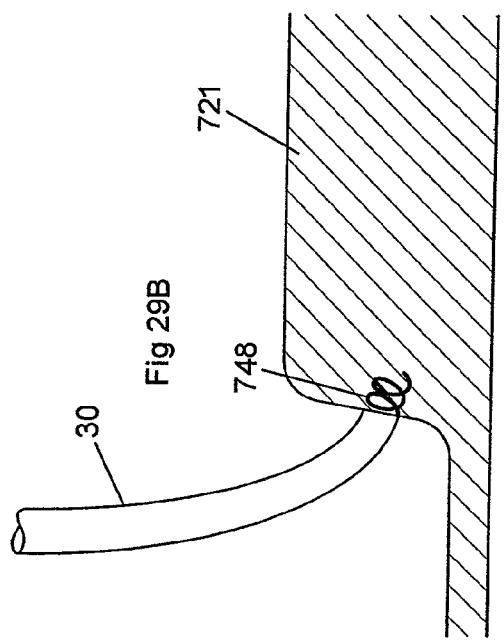

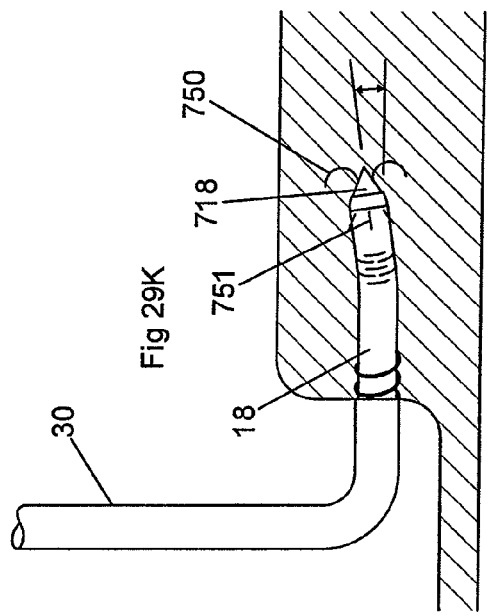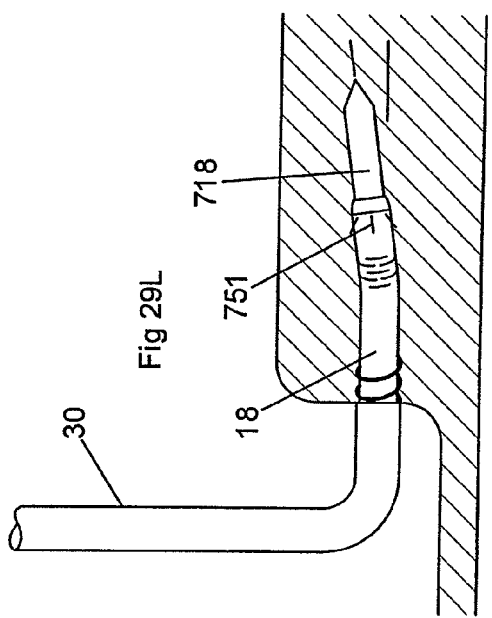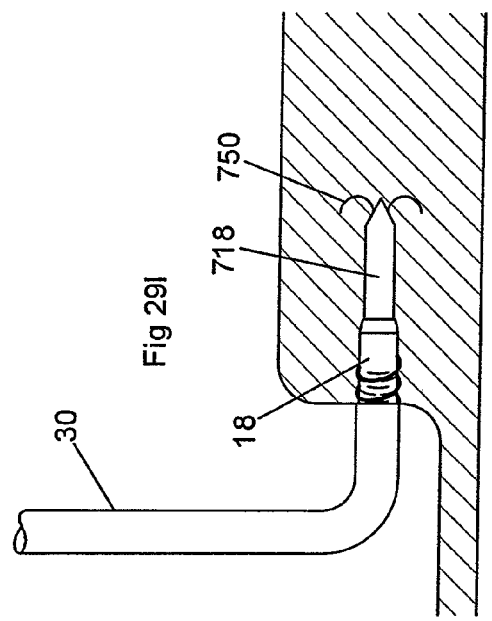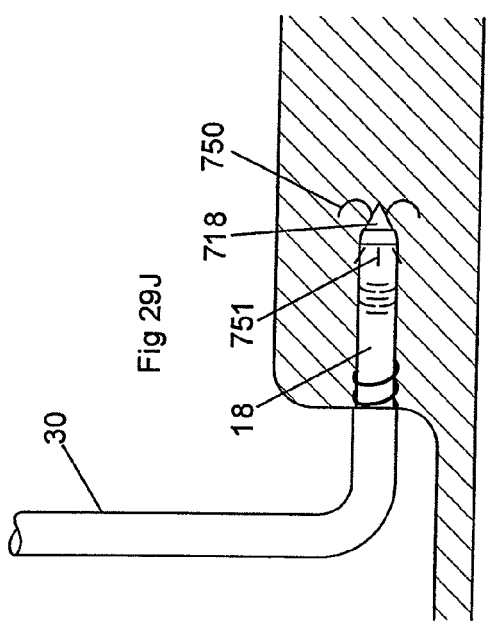

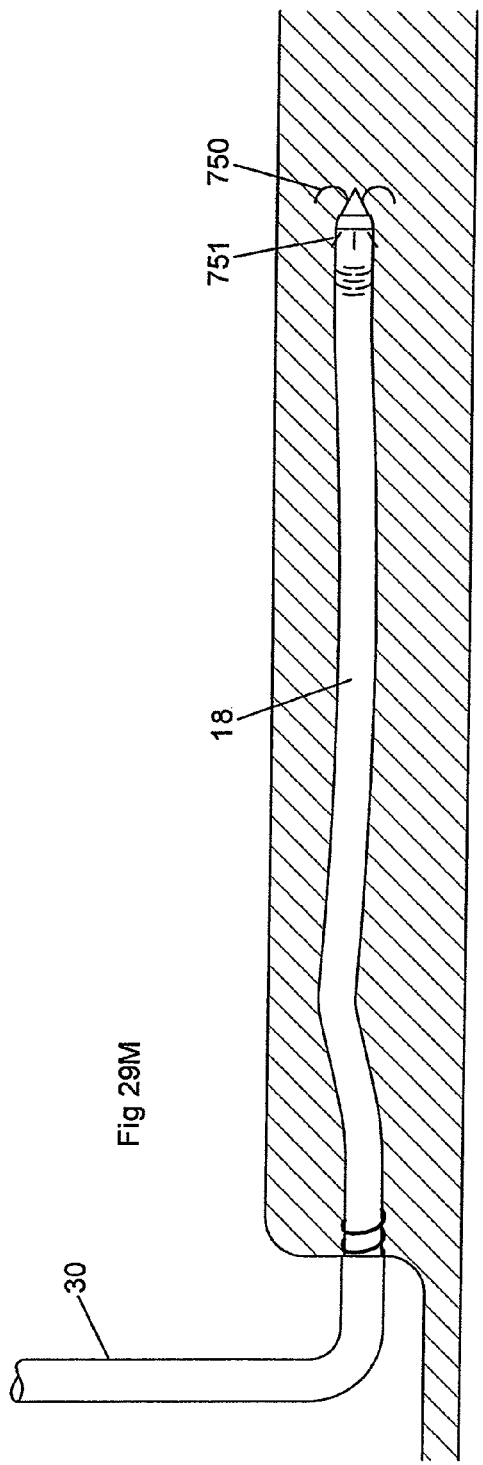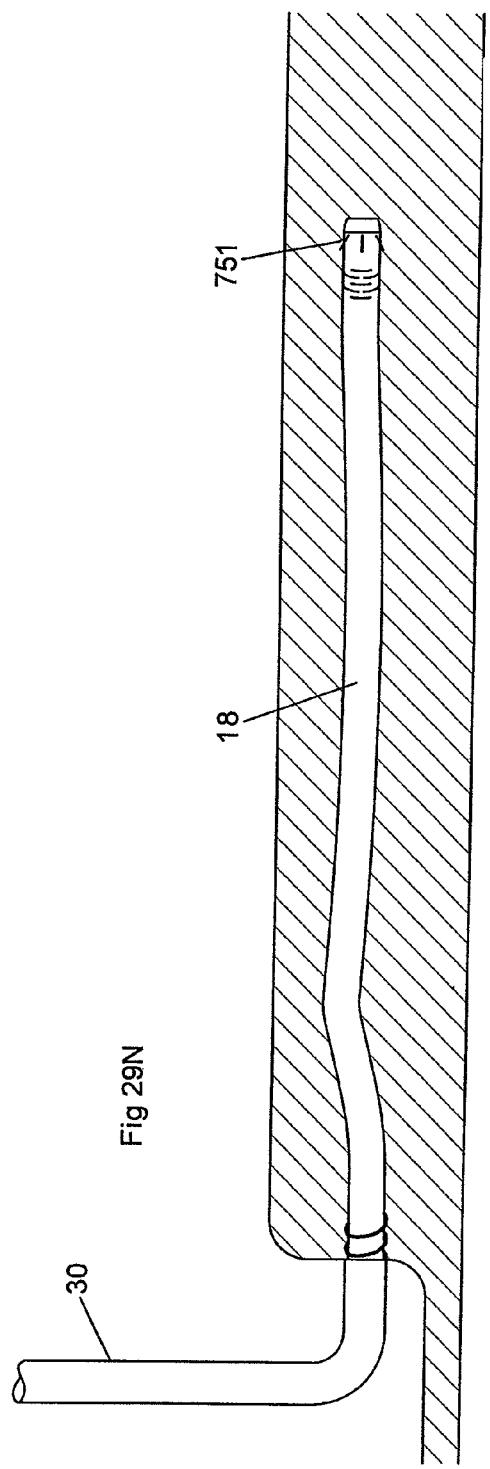

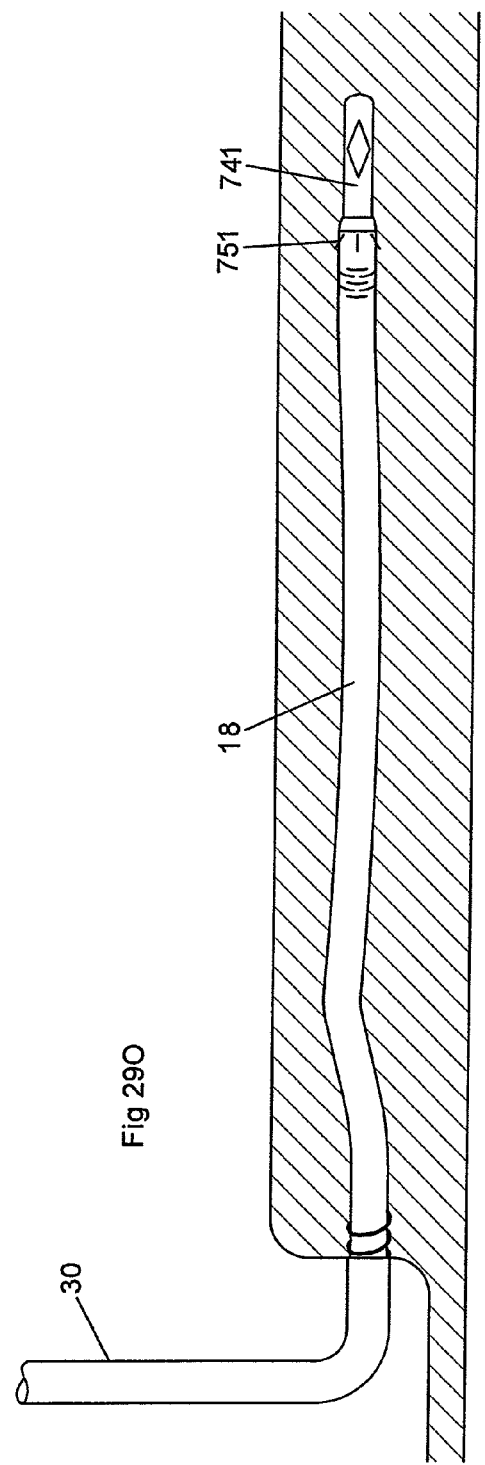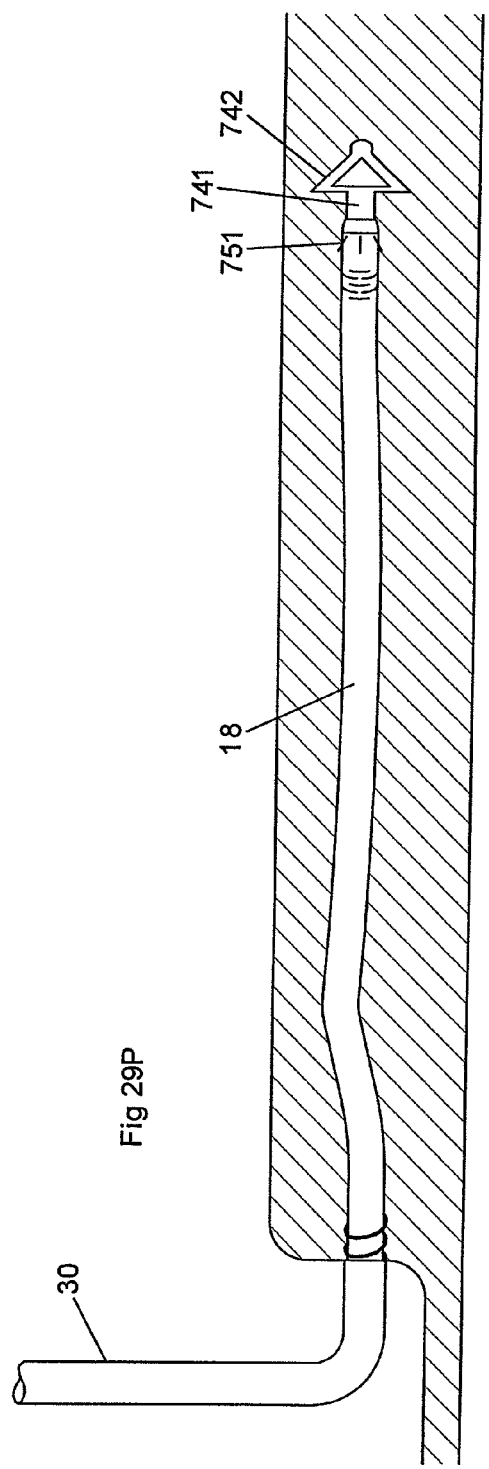

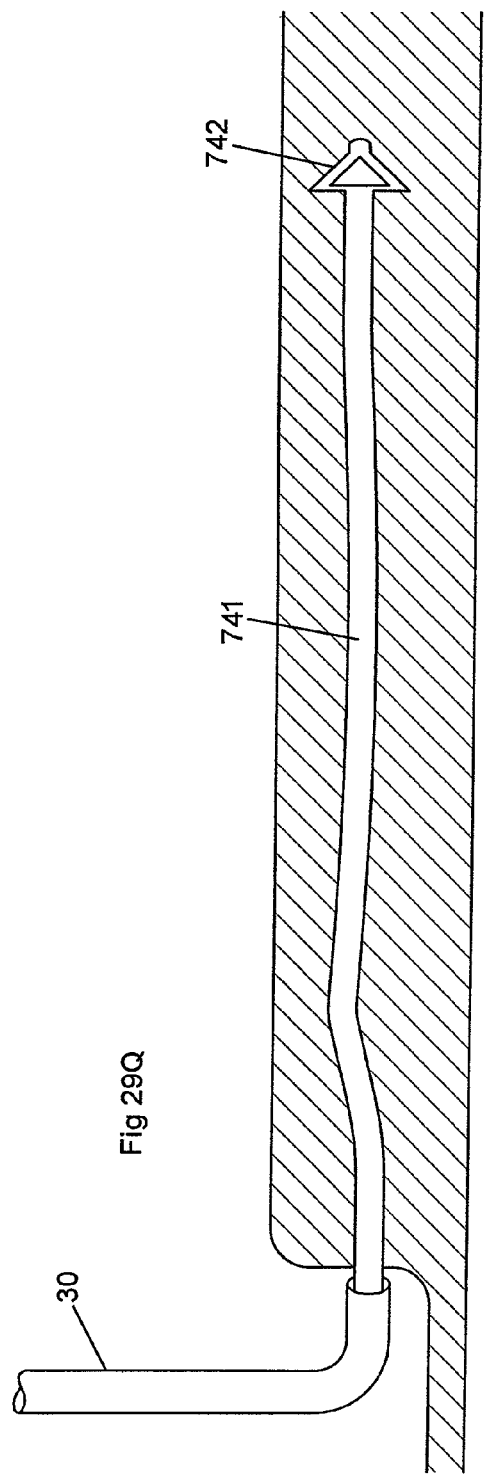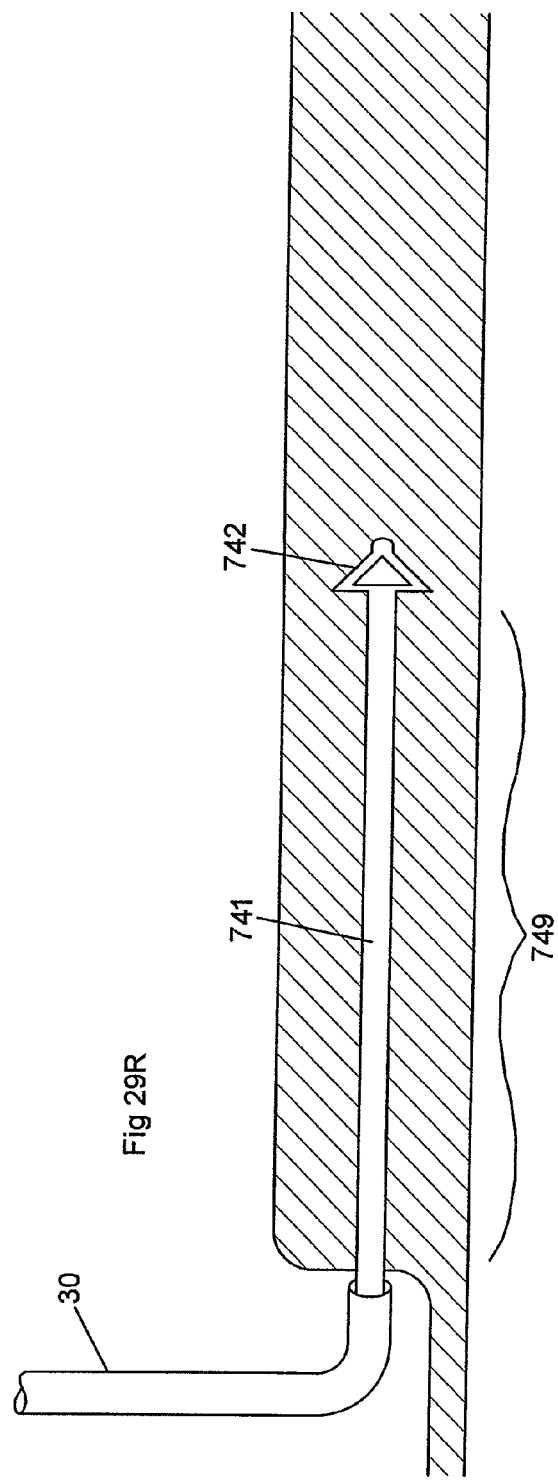

ROBOTICALLY CONTROLLED INTRAVASCULAR TISSUE INJECTION SYSTEM

RELATED APPLICATION DATA

The present application is a continuation of U.S. patent application Ser. No. 11/202,925, filed Aug. 12, 2005, which claims the benefit under 35 U.S.C. §119 to U.S. provisional patent application Ser. Nos. 60/600,869, filed Aug. 12, 2004, 60/644,505, filed Jan. 13, 2005, 60/677,580, filed May 3, 2005, and 60/678,097, filed May 4, 2005. The foregoing applications, along with U.S. patent application Ser. Nos. 11/185,432, filed Jul. 19, 2005, and 11/073,363, filed Mar. 4, 2005, are all hereby incorporated by reference into the present application in their entirety.

FIELD OF INVENTION

The invention relates generally to robotically controlled systems, such as telerobotic surgical systems, and more particularly to a robotic catheter system for performing minimally invasive diagnostic and therapeutic procedures.

BACKGROUND

Robotic surgical systems and devices are well suited for use in performing minimally invasive medical procedures, as opposed to conventional techniques wherein the patient's body cavity is open to permit the surgeon's hands access to internal organs. For example, there is a need for a highly controllable yet minimally sized system to facilitate imaging, diagnosis, and treatment of tissues which may lie deep within a patient, and which may be preferably accessed only via naturally-occurring pathways such as blood vessels or the gastrointestinal tract.

BRIEF DESCRIPTION OF THE DRAWINGS

The drawings illustrate the design and utility of embodiments of the disclosed inventions, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only typical embodiments and are not therefore to be considered limiting of its scope.

FIG. 8B is a schematic view of a system comprising an instrument driver interfaced to an instrument set comprising coaxially-interfaced sheath and guide instruments, which are shown in detail in a magnified inset according to another embodiment of the disclosed inventions.

FIGS. 9A-H are detailed perspective views of hybrid distal tip structures for elongate instruments according to various embodiments of the disclosed inventions.

FIG. 10A is a perspective view of an elongate probe having a proximal mechanical lever for advancing and/or retracting an injection needle according to one embodiment of the disclosed inventions.

FIG. 10B is an exemplary field of view of an imaging device showing a needle or needle/electrode as it is advanced out of a probe according to one embodiment of the disclosed inventions.

FIG. 10C is a schematic view of a needle accessing a mitral annulus from a coronary sinus according to one embodiment of the disclosed inventions.

FIG. 12A is a detailed perspective view of a sheath or guide instrument according to one embodiment of the disclosed inventions.

FIG. 12B is a detailed perspective view of the sheath or guide instrument of FIG. 12A engaged to a tissue mass or wall by vacuum.

FIG. 13A is a detailed perspective view of a sheath or guide instrument having a coil at its distal end according to another embodiment of the disclosed inventions.

FIG. 13B is a detailed perspective view of the sheath or guide instrument of FIG. 13A with a needle tool or instrument protruding from its distal end.

FIG. 15 is a perspective view of a guide instrument having an ultrasound transducer according to one embodiment of the disclosed inventions.

FIG. 16A is a detailed perspective view of a full circumferential array of ultrasound transducers around an instrument according to one embodiment of the disclosed inventions.

FIG. 16B is a detailed axial view of the full circumferential array of FIG. 16A.

FIG. 16C is an exemplary image from the full circumferential array of FIGS. 16A-B.

FIG. 17A is a detailed perspective view of a partial circumferential ultrasound transducers around an instrument according to another embodiment of the disclosed inventions.

FIG. 17B is a detailed axial view of the partial circumferential array of FIG. 17A.

FIG. 17C is an exemplary image set from the partial circumferential array of FIGS. 17A-B.

FIG. 20 is a perspective view of a tissue-traversing needle instrument according to one embodiment of the disclosed inventions.

FIGS. 21A-F are detailed perspective views of tissue-traversing needle instruments according to various embodiments of the disclosed inventions.

FIGS. 23A-B and 25 are perspective views of deployable tension prostheses according to various embodiments of the disclosed inventions.

FIGS. 24A-C are detailed perspective views of anchoring tips for deployable tension prostheses according to various embodiments of the disclosed inventions.

FIG. 26A is a detailed longitudinal cross-sectional view of a slidable flexible housing for a deployable tension prosthesis according to one embodiment of the disclosed inventions.

FIGS. 26B and 27B are detailed perspective views of a slidable flexible housing for a deployable tension prosthesis according to one embodiment of the disclosed inventions.

FIG. 27A is a detailed plan view of a slidable flexible housing for a deployable tension prosthesis according to one embodiment of the disclosed inventions.

FIGS. 28A-B are detailed perspective views of slidable flexible housings for deployable tension prostheses according to various embodiments of the disclosed inventions.

DETAILED DESCRIPTION OF THE ILLUSTRATED EMBODIMENTS

Figure 1:
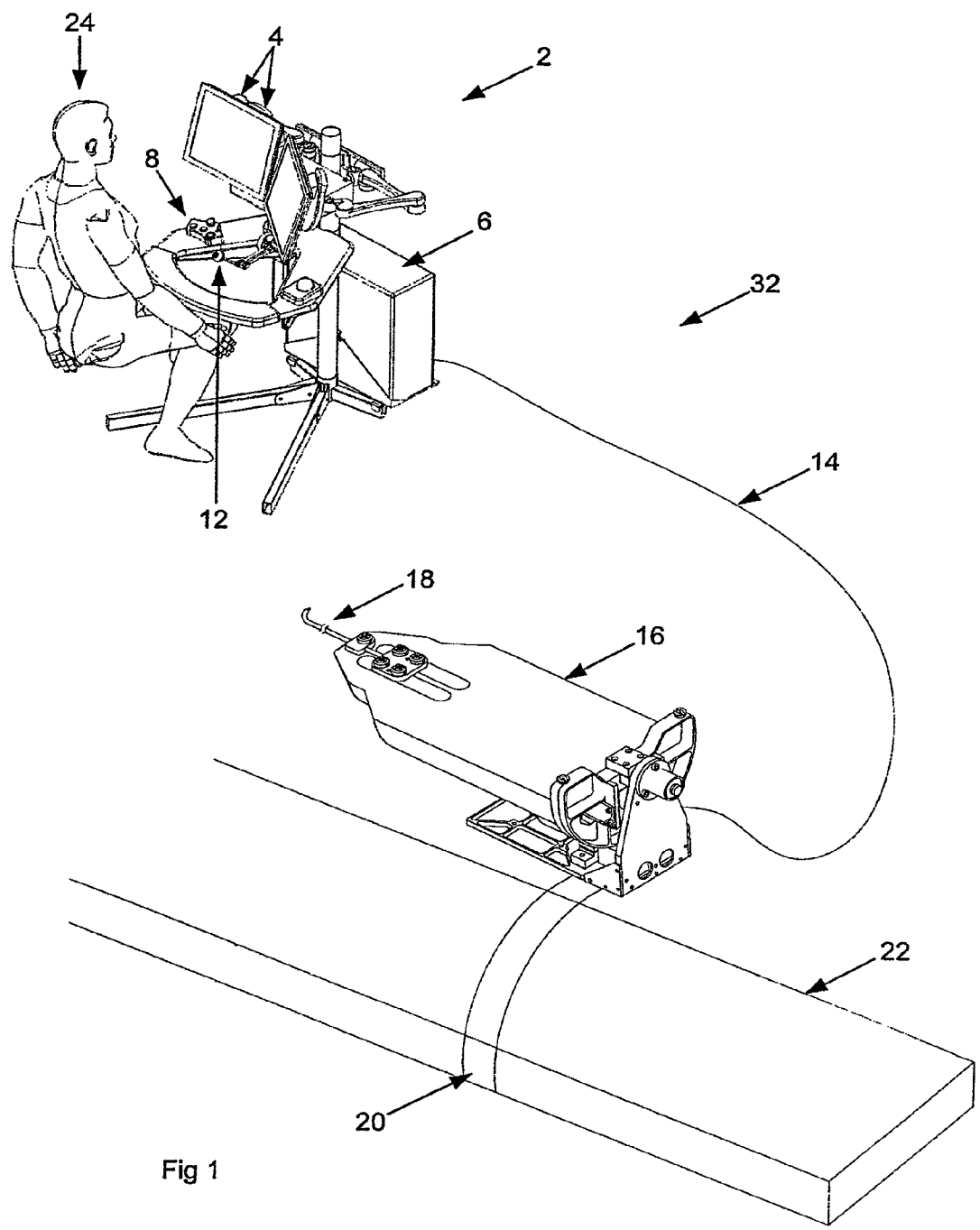
FIG. 1 is a schematic view of a robotic catheter system in accordance with one embodiment of the disclosed inventions.

Referring to FIG. 1, one embodiment of a robotic catheter system 32, includes an operator control station 2 located remotely from an operating table 22, to which a instrument driver 16 and instrument 18 are coupled by a instrument driver mounting brace 20. A communication link 14 transfers signals between the operator control station 2 and instrument driver 16. The instrument driver mounting brace 20 of the depicted embodiment is a relatively simple, arcuate-shaped structural member configured to position the instrument driver 16 above a patient (not shown) lying on the table 22.

Figure 2:
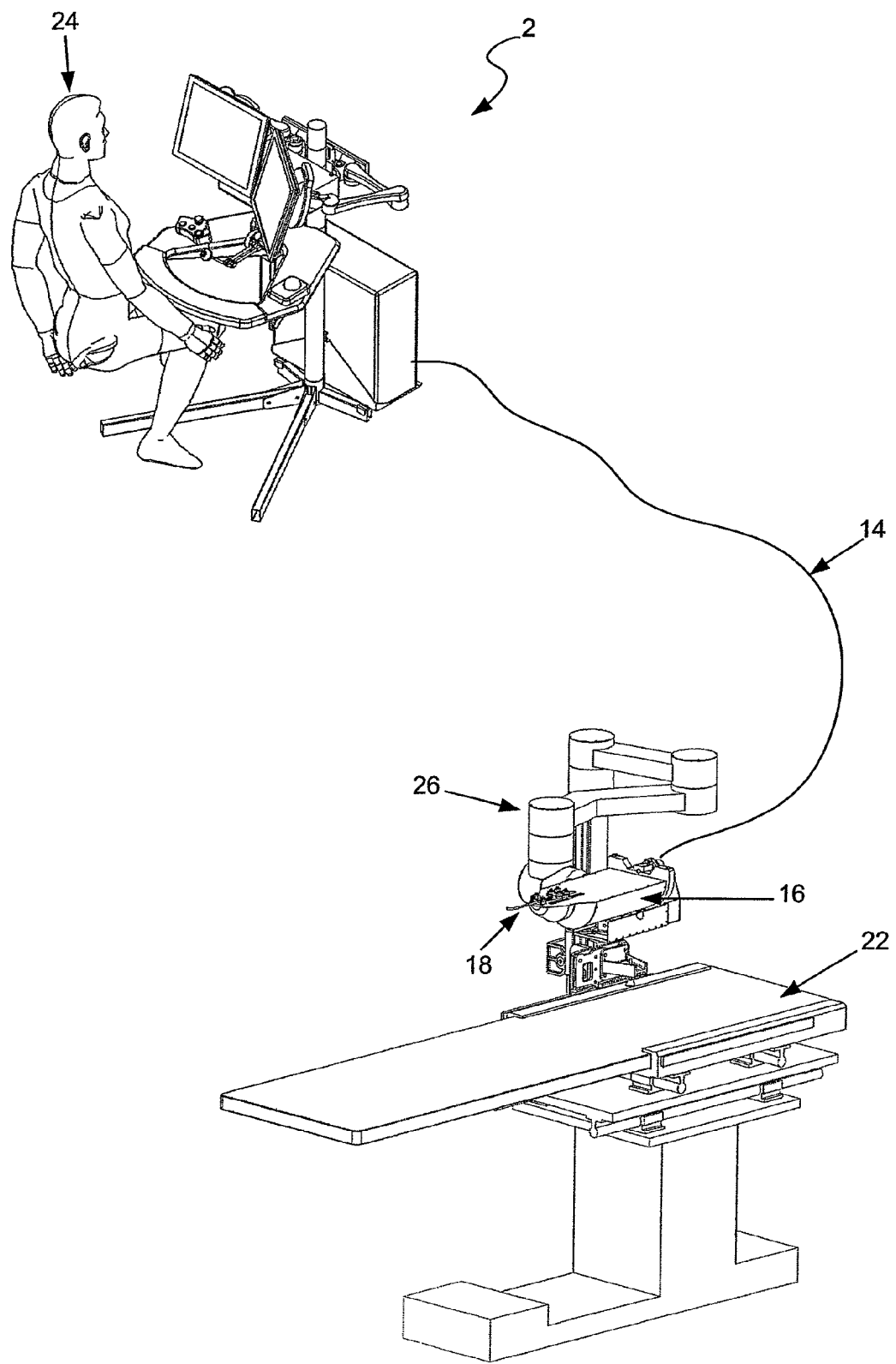
FIG. 2 is a schematic view of a robotic catheter system in accordance with another embodiment of the disclosed inventions.

In FIG. 2, another embodiment of a robotic catheter system is depicted, wherein the arcuate-shaped member 20 is replaced by a movable support-arm assembly 26. The support assembly 26 is configured to movably support the instrument driver 16 above the operating table 22 in order to position the instrument driver 16 for convenient access into desired locations relative to a patient (not shown). The support assembly 26 in FIG. 2 is also configured to lock the instrument driver 16 into position.

Figure 3:
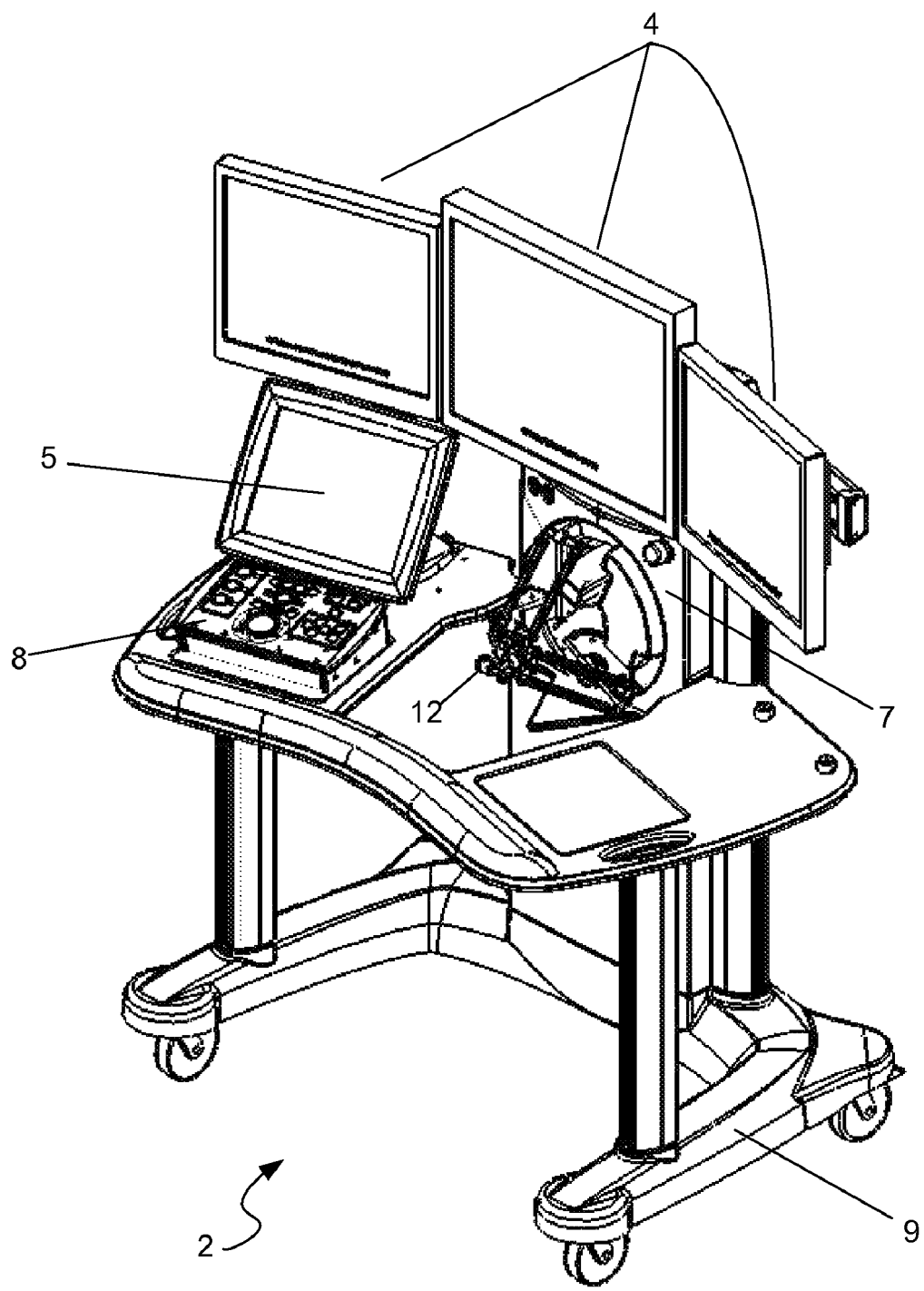
FIG. 3 is a perspective view of an operator control station in accordance with yet another embodiment of the disclosed inventions.
Figure 4:
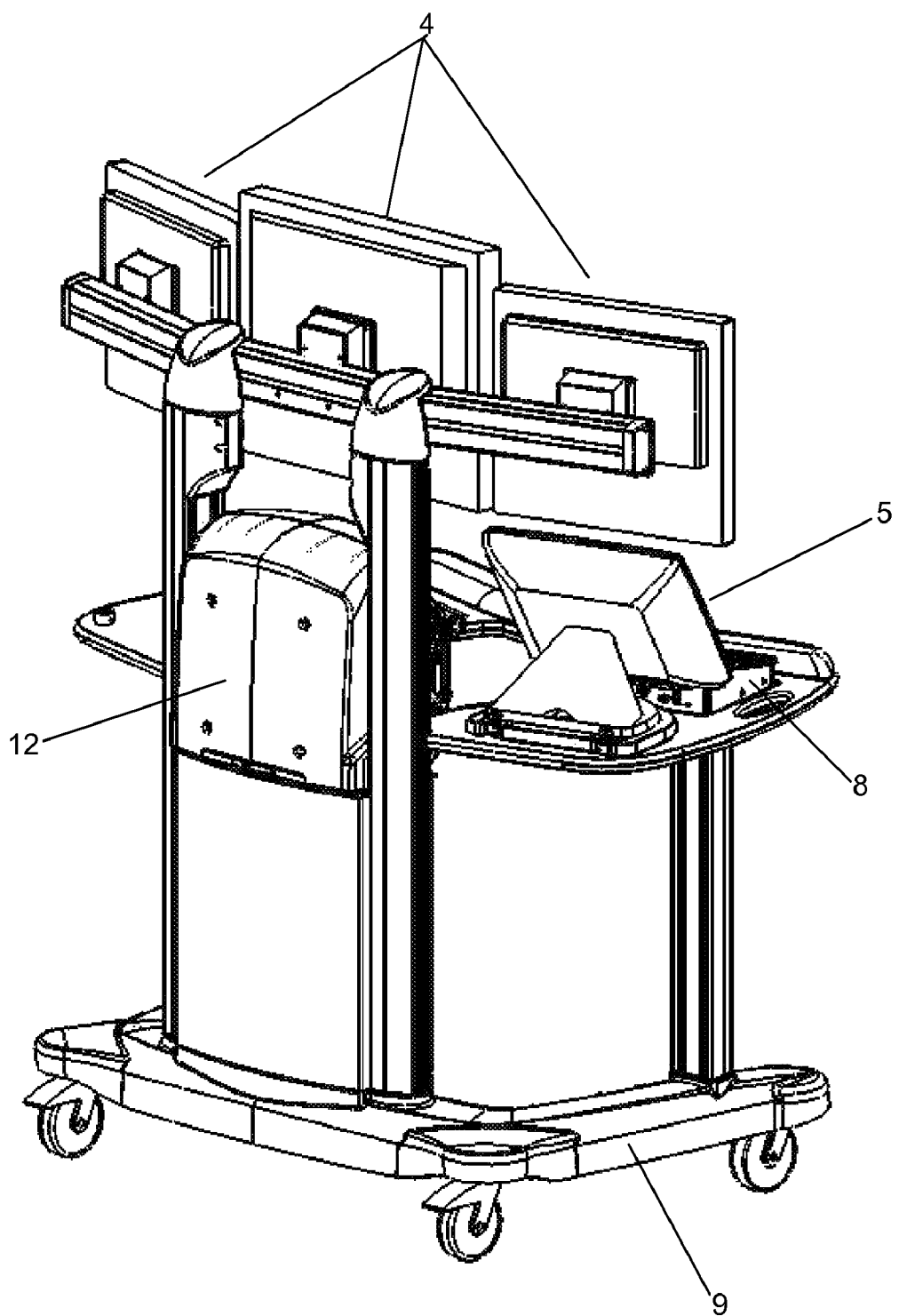
FIG. 4 is a reverse perspective view of the operator control station of FIG. 3.

Referring to FIG. 3, a view of another variation of an operator control station (2) is depicted having three displays (4), a touchscreen user interface (5), and a control button console (8). The master input device (12) depicted in the embodiment of FIG. 3 is depicted and described in further detail in reference to FIG. 105B. Also depicted in the embodiment of FIG. 3 is a device disabling switch (7) configured to disable activity of the instrument temporarily. The cart (9) depicted in FIG. 3 is configured for easy movability within the operating room or catheter lab, one advantage of which is location of the operator control station (2) away from radiation sources, thereby decreasing radiation dosage to the operator. FIG. 4 depicts a reverse view of the embodiment depicted in FIG. 3.

Figure 5:
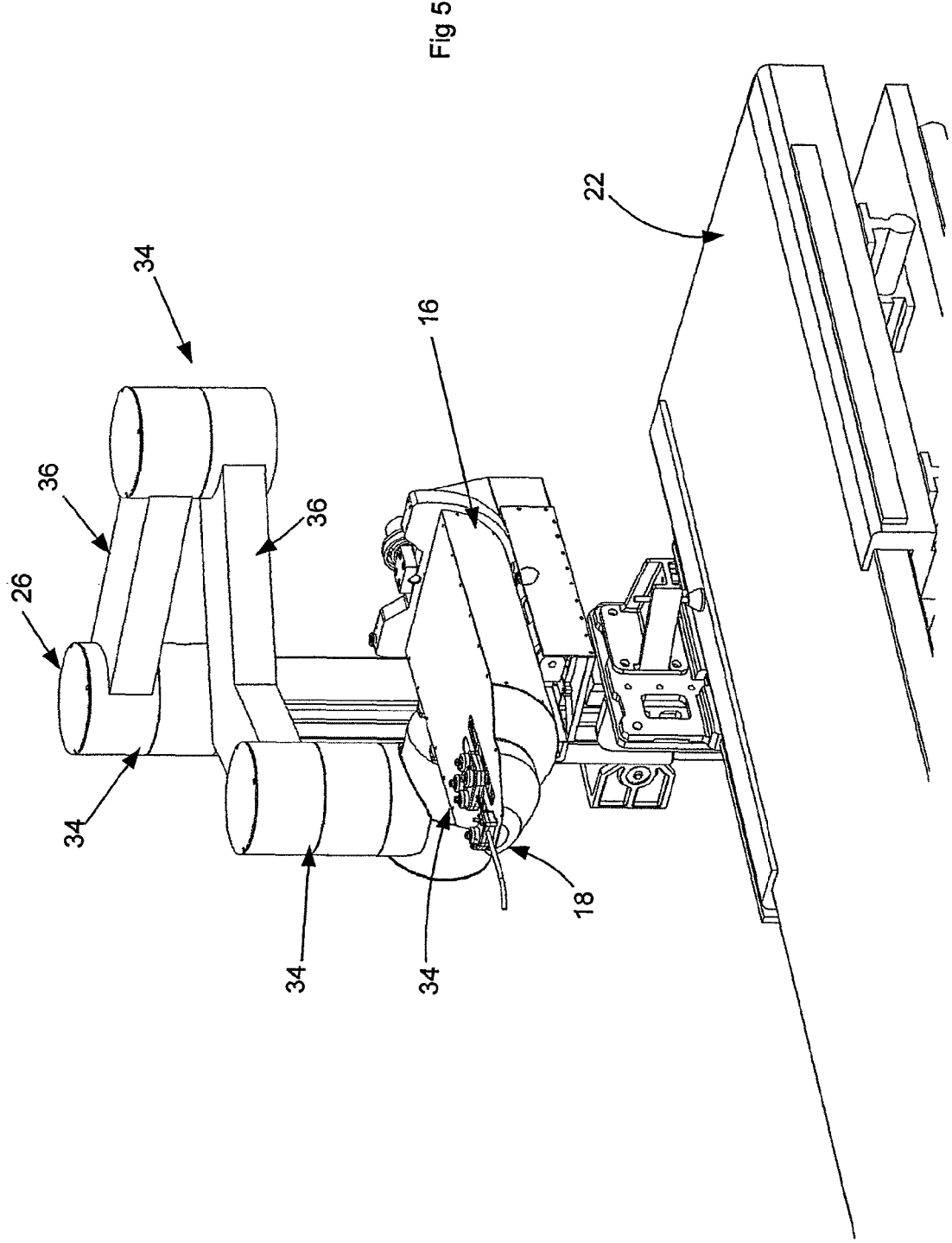
FIG. 5 is a perspective view of portions of a robotic catheter system in accordance with one embodiment of the disclosed inventions, including a support assembly.

FIG. 5 provides a closer view of the support assembly 26 depicted in the embodiment of FIG. 2. The support assembly 26 comprises a series of rigid links 36 coupled by electronically braked joints 34. The joints 34 allow motion of the links 36 when energized by a control system (not shown), but otherwise prevent motion of the links. The control system may be activated by a switch (e.g., a footswitch or thumbswitch), or computer interface. In another embodiment, the rigid links 36 may be coupled by mechanically lockable joints, which may be locked and unlocked manually using, for example, locking pins, screws, or clamps. The rigid links 36 preferably comprise a light but strong material, such as high-gage aluminum, shaped to withstand the stresses and strains associated with precisely maintaining a three-dimensional position of the approximately ten pound weight of a typical embodiment of the instrument driver 16 once the position of the link 36 is fixed.

Figure 6:
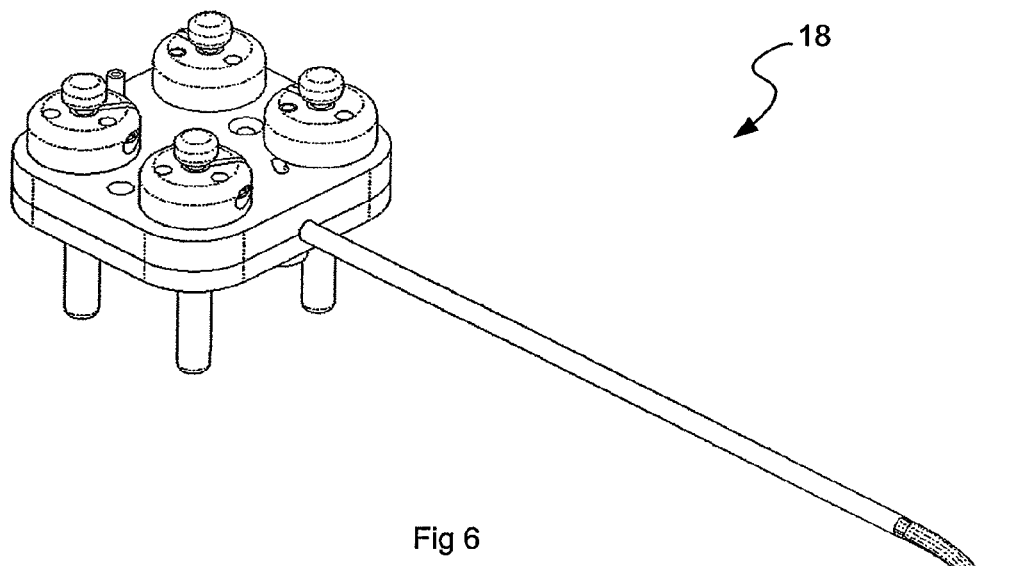
FIG. 6 is an isometric view of the an instrument configured for use with the instrument drivers of FIGS. 1-3 according to one embodiment of the disclosed inventions.
Figure 7:
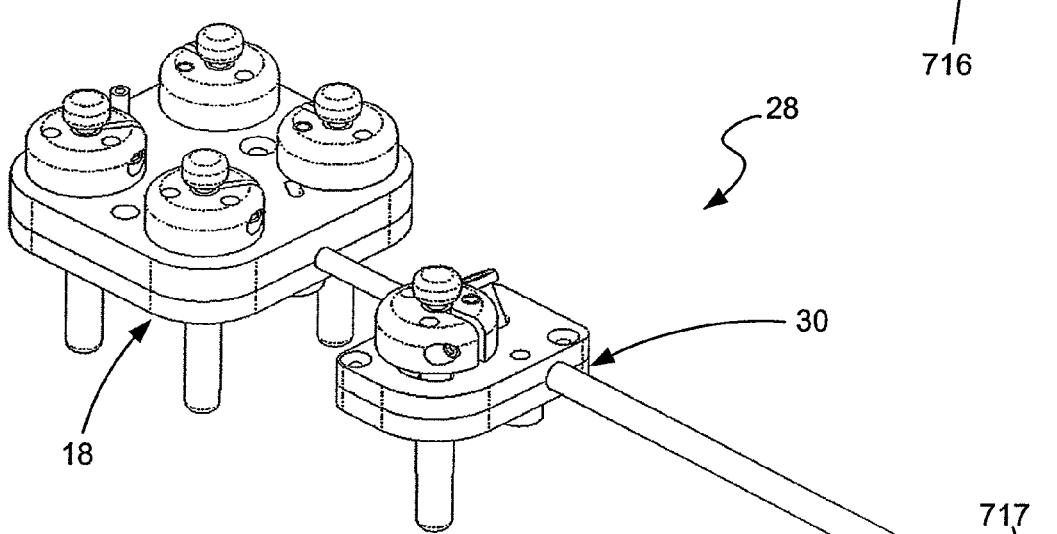
FIG. 7 is an isometric view of the an instrument configured for use with the instrument drivers of FIGS. 1-3 and having a coaxially coupled and independently controllable sheath instrument according to another embodiment of the disclosed inventions.

FIGS. 6 and 7 depict isometric views of respective embodiments of instruments configured for use with an embodiment of the instrument driver (16), such as that depicted in FIGS. 1-3. FIG. 6 depicts an instrument (18) embodiment without an associated coaxial sheath coupled at its midsection. FIG. 7 depicts a set of two instruments (28), combining an embodiment like that of FIG. 6 with a coaxially coupled and independently controllable sheath instrument (30). To distinguish the non-sheath instrument (18) from the sheath instrument (30) in the context of this disclosure, the "non-sheath" instrument may also be termed the "guide" instrument (18). The guide instrument (18) defines an inner lumen (716) through which a tool, such as an ablation catheter, tissue grasper, endoscope, injection needle, or tissue-traversing needle may be deployed. Localization sensors (717), such as those available from Biosense Webster, Endocardial Solutions, Medtronic, and others, may be coupled to or integrated within the sheath instrument (30), guide instrument (18), and any coaxially-associated tools, to provide accurate three-dimensional location information to the computerized robotic system utilized to operate the subject instruments.

Figure 8A:
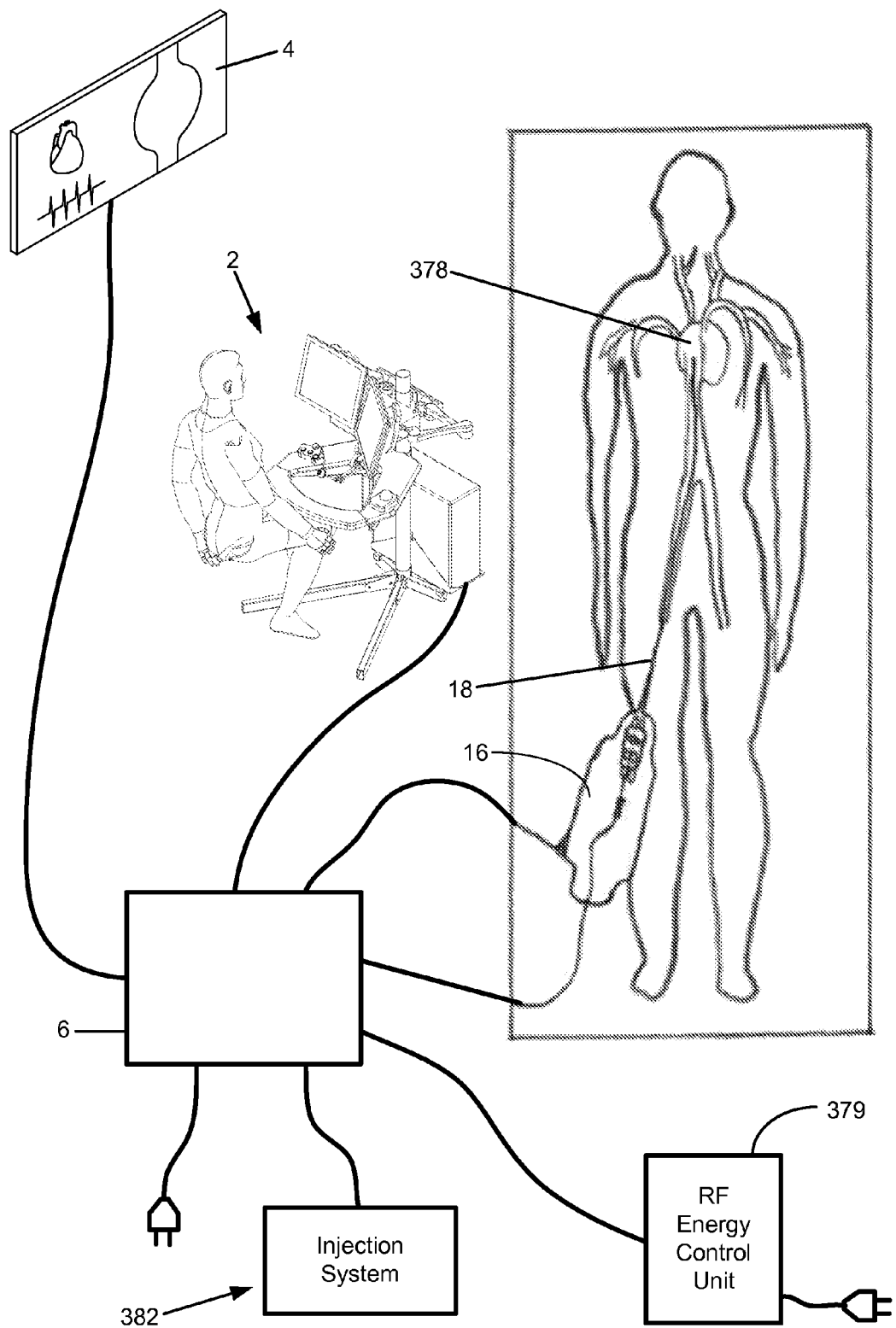
FIG. 8A is a schematic view of a system comprising an operator control station, an instrument driver, a computer or processor, a display monitor, an elongate instrument coupled to an electrode, and an RF energy control unit according to one embodiment of the disclosed inventions.

Referring to FIG. 8A, a system comprising an operator control station (2), an instrument driver (16), a computer or processor (6), a display monitor (4), an elongate instrument (18) coupled to an electrode (378), and an RF energy control unit (379) is depicted. Such a system may be utilized for an embodiment wherein both RF ablation and injection may be conducted—either sequentially or simultaneously. In alternative embodiments, other ablation tools or modalities may be utilized, such as ultrasound or microwave radiation or cryo-ablation, or heated fluids such as hot saline, to facilitate creation of ablative lesions with the distal end of the elongate instrument (18).

Referring to FIG. 8B, a system similar to that depicted in FIG. 8A is depicted comprising an instrument driver (16) interfaced to an instrument set (28) comprising coaxially-interfaced sheath (30) and guide (18) instruments. The guide instrument (18) is coaxially interfaced, through its inner lumen, with an elongate probe (380) which may comprise a heating and/or injecting tool at its distal tip (381). In an embodiment comprising an injecting tip, an injection system (382) may be coupled to the instrument set (28) and configured to controllably deliver fluids, solutions, etc. —such as a biologically-compatible fixative formulation such as genepin, cells, such as stem cells, skeletal myoblasts, cardiac muscle cells or myoblasts, hormones, medicines, vascular endothelial growth factor, etc., through the injecting tip distally.

Figure 9F:
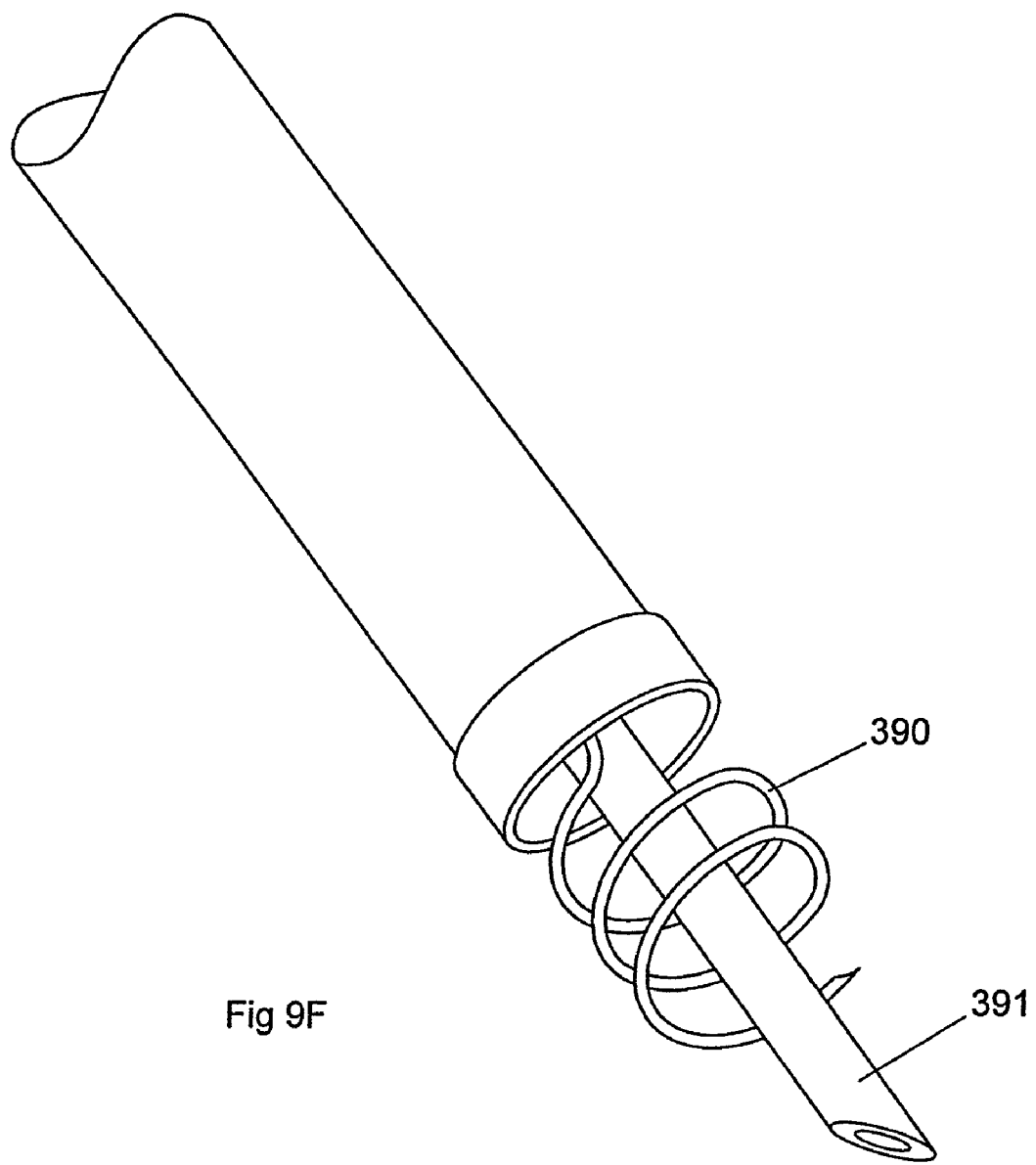

Referring to FIGS. 9A-H, various hybrid distal tip structures for an elongate instrument configured to both inject a chemical solution, such as a genepin solution or solution of another fixative, and also apply RF energy to induce localized denaturation are depicted. FIG. 9A depicts a needle-less injection port (384) positioned through the center of a monopolar RF electrode (383). FIG. 9B depicts a series of needle injection ports (385) located upon an RF electrode (383) for a volumic injection into a broader volume that would be practicable with a single needle.

FIG. 9C depicts an extensible/retractable needle (386) injection port through the center of an RF electrode (383). FIG. 9D depicts bipolar electrode configuration wherein each of two distal elements (387) comprises both an electrode and an injection tip. FIG. 9E depicts a single injection needle through the center of an RF electrode (383), the needle (388) comprising multiple fluid pathways (389) along its length to facilitate a distributed injection through a depth of targeted tissue. The needle (388) may be extensible/retractable, as with each of the distal tip needle structures depicted herein. FIG. 9F depicts an embodiment wherein an injection needle (391) is oriented through the center of a helical structure (390), and wherein any of the distal elements may be an RF electrode—in other words, the injection needle (391) or helical structure (390) may be a monopolar electrode, or each may be an electrode in a bipolar configuration.

FIG. 9G depicts an embodiment wherein a bullet-shaped electrode (392) is positioned through at least a portion of a helical injection needle (393). FIG. 9H depicts an embodiment similar to that of FIG. 9G with the exception that a distal ring (394) comprises the electrode as opposed to the bullet-shaped electrode of FIG. 9G. The helical injection needles of the embodiments depicted in FIGS. 9G and 9H may have side ports (not shown) as depicted in the embodiment of FIG. 9E, and may comprise an electrode form a bipolar electrode configuration in association with the bullet-shaped electrode (392) or ring electrode (394). In other variations configured for injection without RF energy delivery, geometries such as those depicted in FIGS. 9A-H may be utilized, absent the RF electrode hardware at the distal tip. Conventional injection needle tips may also be utilized for precision injection without RF delivery through the working lumen of the subject robotic catheter instruments.

Referring to FIGS. 10A-C, a retractable injection needle (395) may be retractably extended from the side of an elongate probe (397) to provide access to tissue structures located to the periphery of a given probe orientation, such as the mitral annulus as oriented from the coronary sinus, as depicted in FIG. 10C. The injection needle (395) may be advanced and/or retracted utilizing a simple proximal mechanical lever (396), as depicted in FIG. 10A, or may be associated with an electromechanical configuration for precisely actuating advancement and/or retraction.

To facilitate accurate positioning of a side-extending injector, or injector which also comprises an electrode in another embodiment, an imaging device (398), such as an ultrasound array, CCD device, or more conventional optical camera, in one embodiment comprising a mirror for side-oriented field of view (403), may be coupled to the probe (397) to provide a field of view (403) configured to capture images of at least a portion of the needle or needle/electrode as it is advanced out of the probe (397), as depicted in FIG. 10B. Referring to FIG. 10C, a partial cross sectional view of a system such as that depicted in FIGS. 10A and 10B is depicted with the probe (397) threaded down a coronary sinus (401) of a human heart, and an injection needle (395), in this embodiment also comprising an electrode, directed out of the coronary sinus (401) lumen and into the collagenous mitral valve annulus (604). The field of view (403) of the imaging device (398), in the depicted embodiment comprising an ultrasound transducer, is oriented to capture images of at least a portion of the needle (395), and preferably portions of surrounding identifiable tissues, such as the mitral annulus (604) or mitral valve leaflet (605).

Utilizing instruments such as those depicted in FIGS. 8-10, precision injection therapy may be conducted. For example, in one embodiment, a system such as that depicted in FIGS. 8A-B, absent the RF electrode and energy system, may be utilized to navigate an injection tip from the inferior vena cava or superior vena cava into the right atrium of the heart where a precision injection may be conducted. Crossing the tricuspid valve, a precision injection may be conducted in the right ventricle. Alternatively, a robotically-operated guide instrument may be navigated to the left heart via a trans-septal puncture, or via a retrograde approach through the aorta and into the left ventricle. Precision robotic control of the guide and sheath instruments facilitates precision placement of injection tips to controllably deliver fluids, solutions, etc—such as a biologically-compatible fixative formulation such as genepin, cells, such as stem cells, skeletal myoblasts, cardiac muscle cells or myoblasts, hormones, medicines, vascular endothelial growth factor, etc.

Figure 11A:
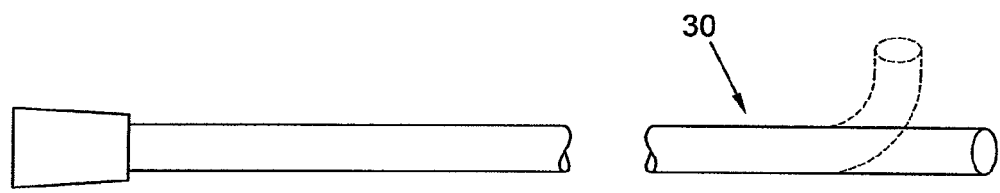
FIG. 11A is a perspective view of a steerable sheath instrument according to one embodiment of the disclosed inventions.
Figure 11B:
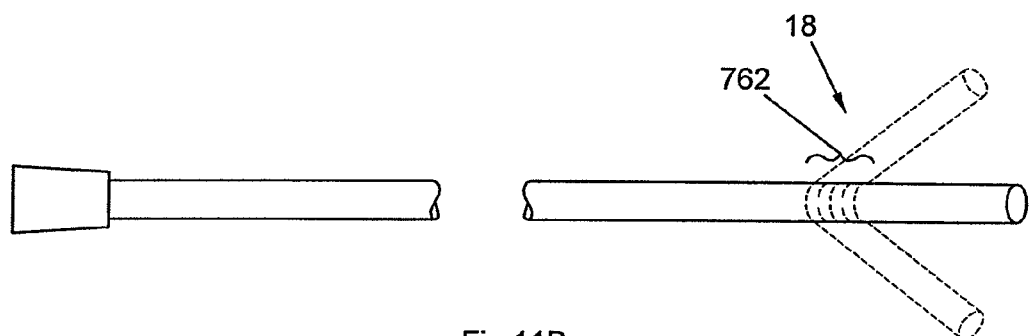
FIG. 11B is a perspective view of a steerable guide instrument according to another embodiment of the disclosed inventions.
Figure 11C:
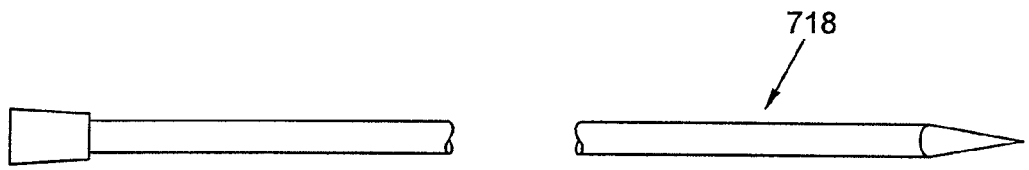
FIG. 11C is a perspective view of a needle instrument or tool according to yet another embodiment of the disclosed inventions.
Figure 11D:
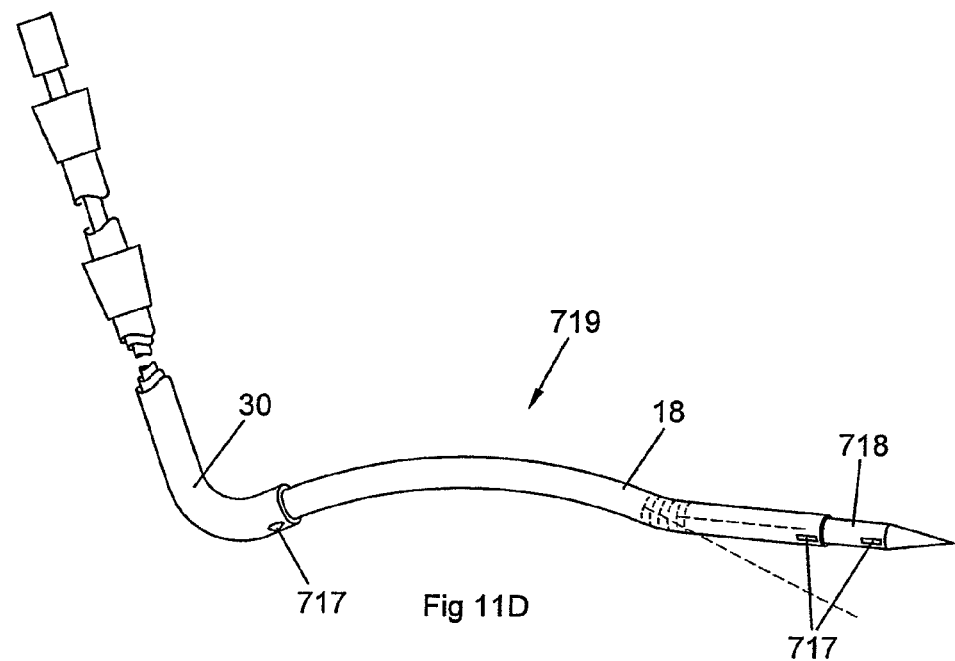
FIG. 11D is a perspective view of a coaxial assembly of the instruments of FIGS. 11A-C.

Referring to FIG. 11A, a steerable sheath instrument (30) is depicted. Referring to FIG. 11B, a steerable guide instrument (18) is depicted, this embodiment having a discrete zone (762) which may be biased to bend more than the adjacent zones through the use of a more flexible structural cross section in such zone. Referring to FIG. 11C, a needle instrument or tool (718) is depicted that is configured for traversing soft tissue such as cardiac muscle tissue when advanced forward. Referring to FIG. 11D, a coaxial assembly (719) of the instruments depicted in FIGS. 11A-C is depicted. In the depicted embodiment, localization sensors (717) are coupled to each of the instruments for accurate determination of relative and absolute positioning.

Referring to FIGS. 12A and 12B, vacuum (720) may be utilized to engage a sheath or guide instrument adjacent a tissue mass or wall (721). Referring to FIGS. 13A and 13B, a helical coil (748) tip may be utilized to rotatably engage an adjacent tissue mass or wall as a needle tool or instrument (718) is forwarded through the working lumen of the associated sheath (30) or guide (18) instrument.

Figure 14A:
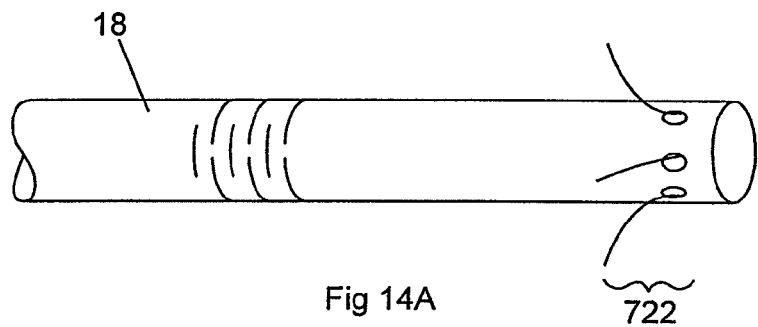
FIGS. 14A-D are detailed perspective views of the distal ends of sheath or guide instruments according to various embodiments of the disclosed inventions.
Figure 14B:
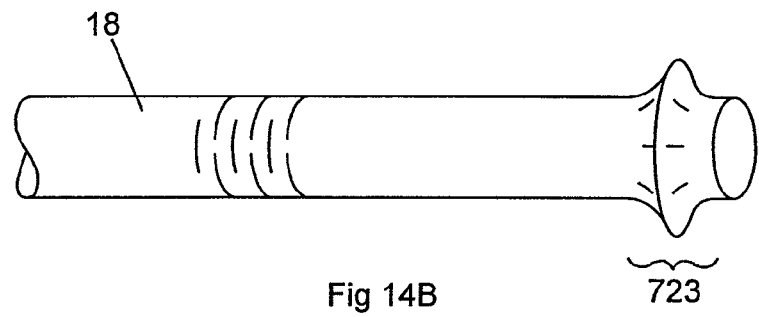
Figure 14C:
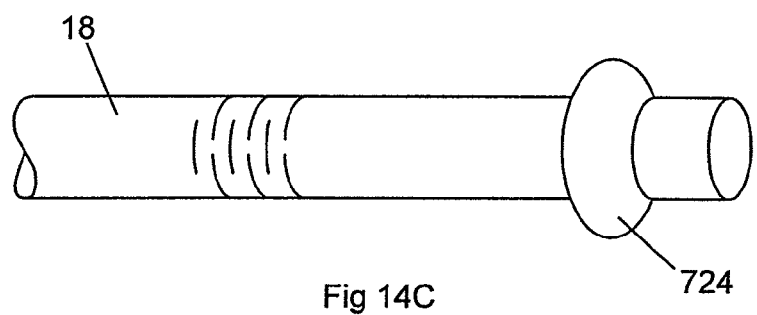
Figure 14D:
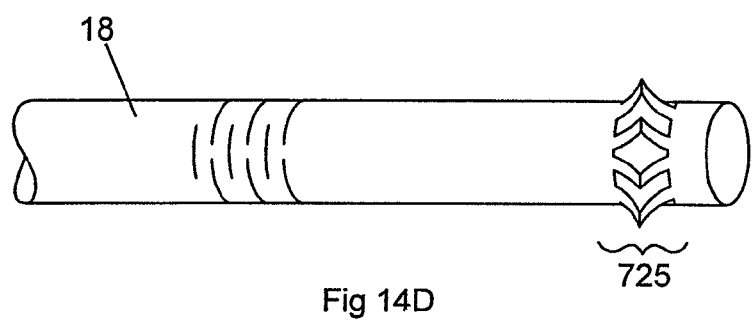

Referring to FIGS. 14A-D, various anchoring mechanisms may be utilized to engage adjacent tissue masses or walls, such as the outwardly-angled barbs (722) depicted in the embodiment of FIG. 14A, the outwardly-expandable circumferential geometry (723) of the embodiment of FIG. 14B, and the expandable balloon (724) of the embodiment of FIG. 14C. FIG. 14D depicts an embodiment similar to that depicted in FIG. 14B with the exception that stress relief cutouts are defined in the expandable geometry (725).

Referring to FIG. 15, a guide (18), sheath (not shown), or needle (not shown) instrument may be outfitted with ultrasound transducers (726) to image adjacent tissue structures and/or other instruments. Referring to FIGS. 16A-C, a circumferential array (727) of ultrasound transducers, such as that available from Volcano Therapeutics, Inc., may be utilized to provide images (728) around the circumference of an instrument. Referring to FIGS. 17A-C, a subset of a full circumferential array may also be utilized to provide a partial circumferential ultrasound image view (729). Referring to FIGS. 18A-D, imaging transducers (727) may be positioned upon a guide instrument, sheath instrument, or both, in addition to upon a needle instrument.

Figure 18A:
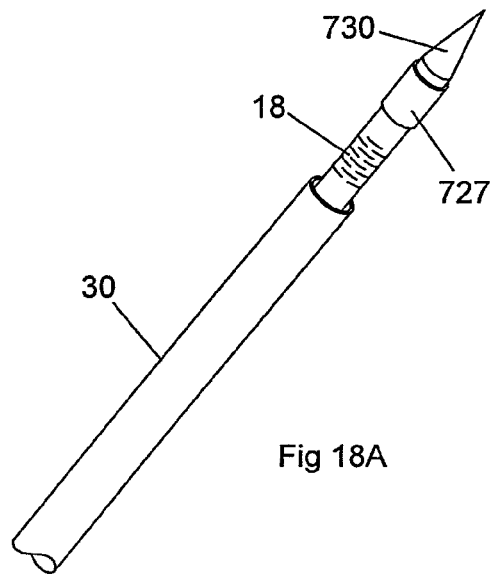
FIG. 18A is a detailed perspective view of a guide instrument with an integrated needle tip and an imaging transducer coupled thereto according to one embodiment of the disclosed inventions.
Figure 18B:
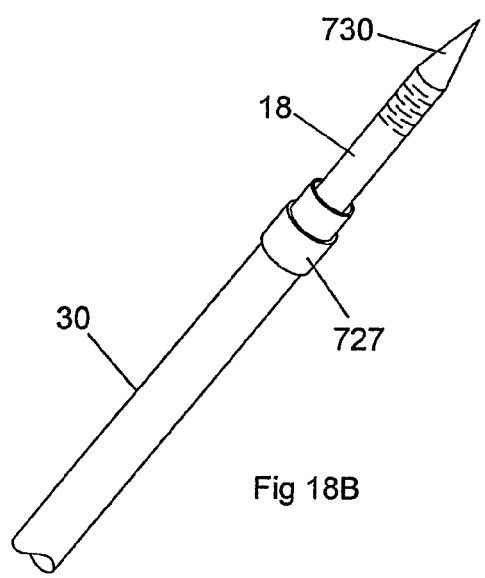
FIG. 18B is a detailed perspective view of a guide instrument with an integrated needle tip and an imaging transducer coupled to an associated sheath according to another embodiment of the disclosed inventions.
Figure 18C:
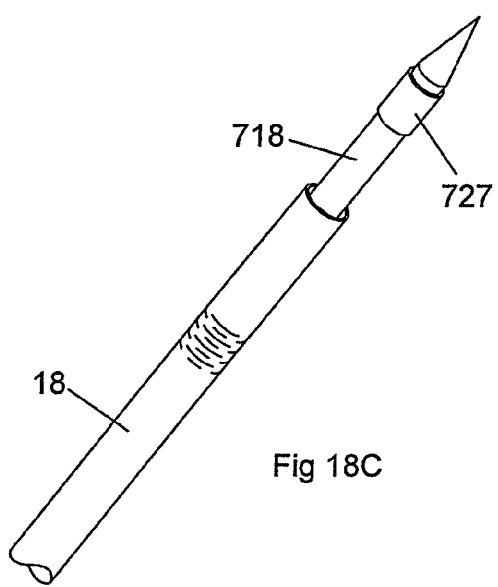
FIG. 18C is a detailed perspective view of a needle instrument deployed through the working lumen of a guide instrument and an imaging transducer coupled thereto according to one embodiment of the disclosed inventions.
Figure 18D:
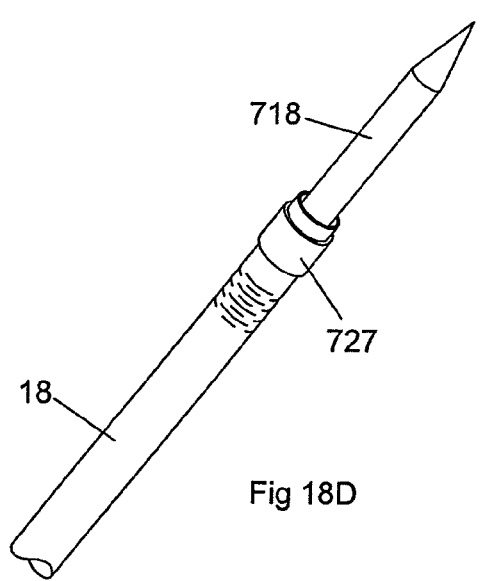
FIG. 18D is a detailed perspective view of a needle instrument deployed through the working lumen of a guide instrument and an imaging transducer coupled to a steerable guide instrument according to another embodiment of the disclosed inventions.
Figure 19:
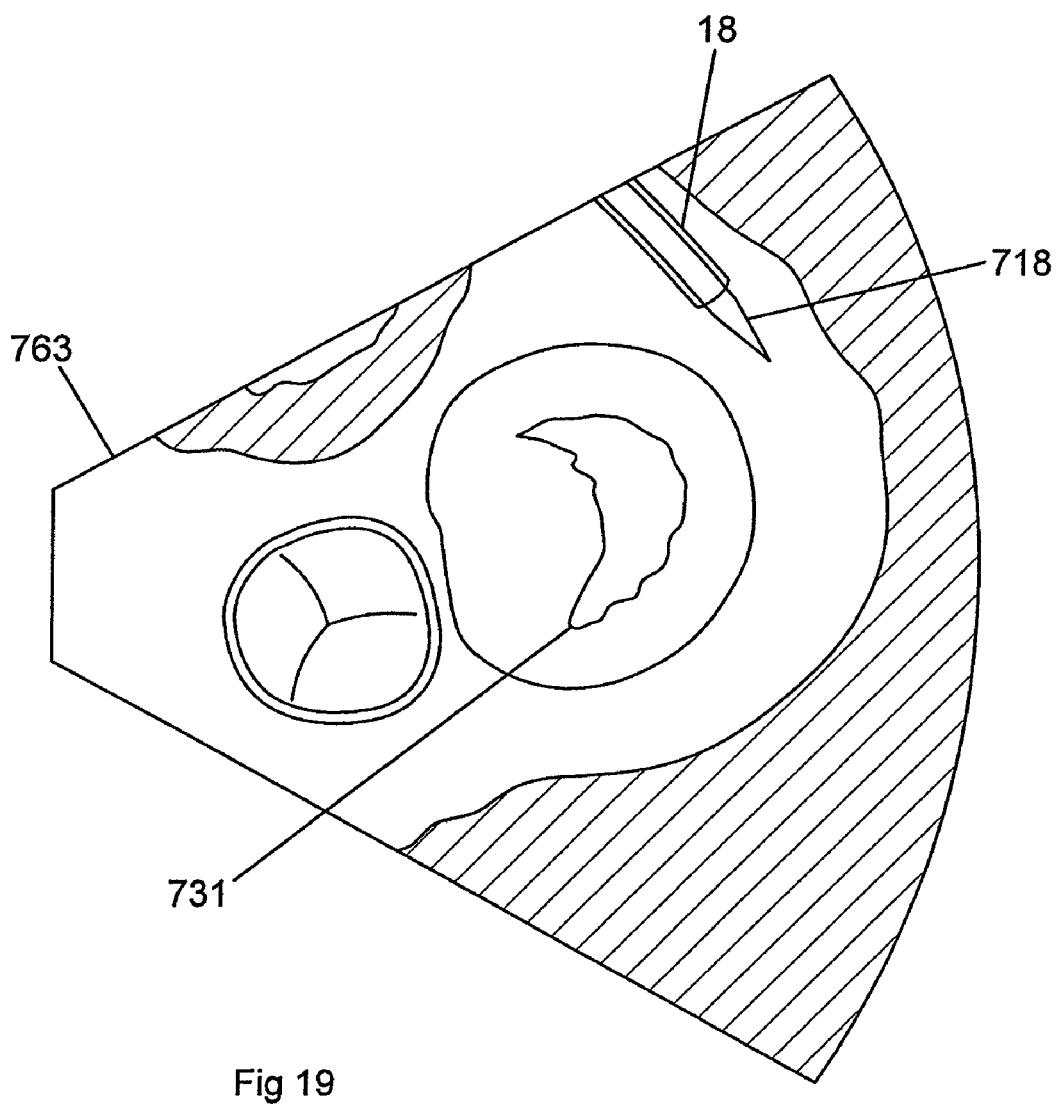
FIG. 19 is an exemplary conventional intracardiac echo or intravascular ultrasound image showing an instrument according to one embodiment of the disclosed inventions.

FIG. 18A depicts an embodiment wherein an imaging transducer is coupled to a guide instrument (18) which has an integrated needle tip (730). FIG. 18B depicts an embodiment similar to that of FIG. 18A with the exception that the imaging transducer (727) is coupled to an associated sheath instrument (30). FIG. 18C depicts an embodiment wherein an imaging transducer (727) is coupled to a needle instrument (718) deployed through the working lumen of a guide instrument (18). FIG. 18D depicts an embodiment similar to that of FIG. 18C with the exception that an imaging transducer (727) is coupled to the steerable guide instrument (18). Referring to FIG. 19, conventional intracardiac echo ("ICE") or intravascular ("IVUS") ultrasound also may be utilized to image (763) pertinent tissue structures (731) and instruments (718, 18).

Referring to FIGS. 20 and 21A-F, various embodiments of suitable tissue-traversing needle instruments (718) are depicted. FIG. 20 depicts a needle instrument (718) with a conventional sharp tip. FIGS. 21A-F depict needle instrument embodiments having controllable mechanisms for at least temporarily anchoring a needle distal tip relative to adjacent tissue structures. FIGS. 21A-C depict embodiments having deployable barbs (732, 733, 734). FIG. 21D depicts circumferentially expandable portions (735) which expand outward as the very distal portion is pulled proximally with a tension member or spring biasing (not shown). FIG. 21E depicts radially expandable members (736) deployed distally, while FIG. 21F depicts an expandable balloon (724) coupled to the distal end of a needle instrument tip.

Figure 22A:
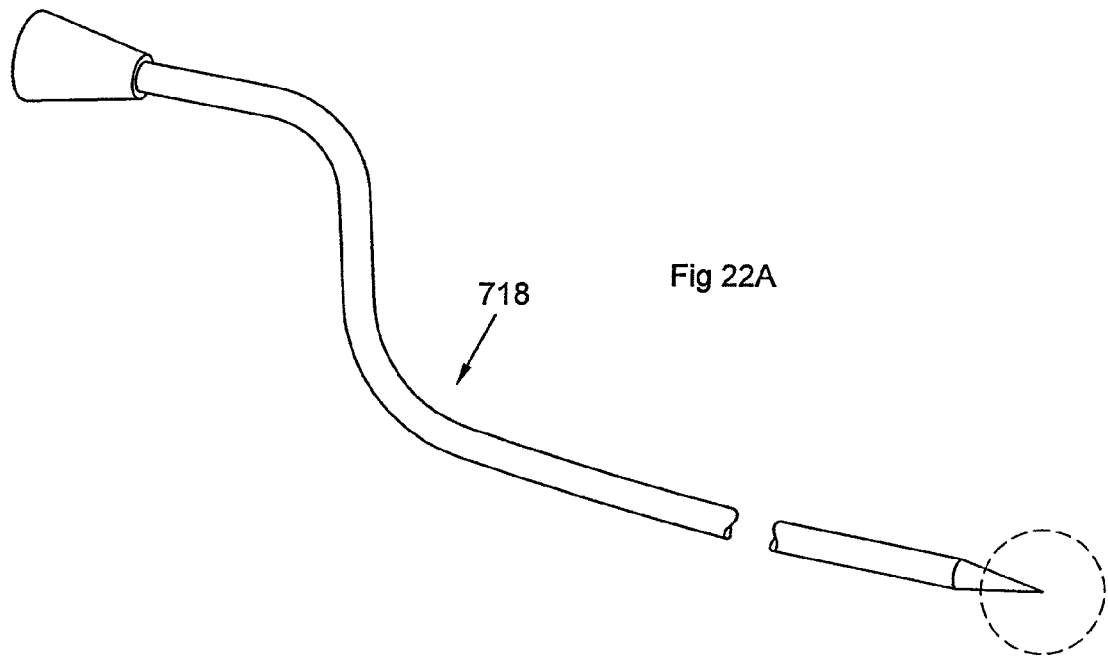
FIG. 22A is a perspective view of a tissue-traversing needle instruments with an injection tip according to one embodiment of the disclosed inventions.
Figure 22B:
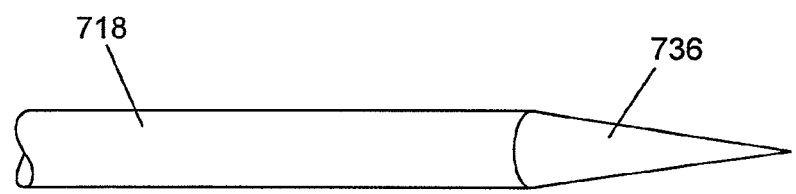
FIGS. 22B-D are detailed perspective views of tissue-traversing needle instruments with injection tips according to various embodiments of the disclosed inventions.
Figure 22C:
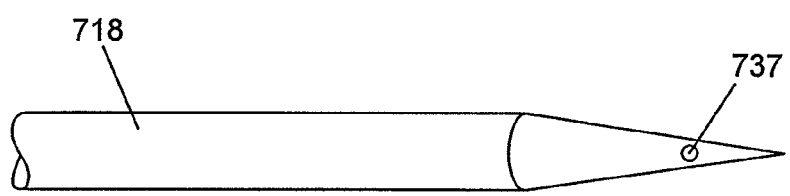
Figure 22D:

Referring to FIGS. 22A-22D, various injection tips are depicted for suitable tissue-traversing needle instrument (718) embodiments. FIG. 22B depicts a sharp traversing tip such as that depicted in FIG. 20 with the exception that the tip defines an injection lumen and port (736). The embodiment of FIG. 22C is similar with the exception that the injection port (737) is positioned proximal of the distal tip. The embodiment of FIG. 22D is similar with the exception that an additional smaller injection needle tip (738) is positioned distal of the distal tip of the tissue-traversing needle, for injections deeper than desired traversing.

Referring to FIGS. 23A-28B, various aspects of various embodiments of deployable tension prostheses (741) are depicted. Referring to FIG. 23A, a deployable tension prosthesis (741) with straight length "l" is depicted coupled to a flexible elongate instrument. The prosthesis has proximal and distal tissue anchors (743, 742). FIG. 23B depicts the prosthesis (741) without the proximal instrument, and shows that the prosthesis preferably is highly flexible.

FIGS. 24A-C depict anchoring tip (742) embodiments for various deployable tension prostheses which may be utilized to retain the position of the distal tip of a deployable tension prosthesis relative to surrounding tissues as the more proximal portions of the deployable tension prosthesis are pulled into tension by a needle instrument proximally. FIG. 24A depicts a barbed tip (745). FIG. 24B depicts a helical tip (746) which may be wound into adjacent tissue structures. FIG. 24C depicts a more broad helical tip (747) which may be utilized to wind into adjacent tissue structures or through holes, defects, or fossas in adjacent tissue structures. FIG. 25 depicts a deployable tension prosthesis (741). When the proximal loop of the tension element (740) depicted in FIG. 25 is pulled in tension relative to the slidable flexible housing (744), proximal (743) and distal (742) expandable members protrude outward anchoring the prosthesis distally and proximally, enabling application of compression to tissue structures positioned adjacent or between the distal and proximal expandable members. Referring to FIGS. 26A-B and 27A-B, the slidable flexible housing (744) may comprise a substantially round or substantially circular cross section. Referring to FIGS. 28A-B, the slidable flexible housing (744) may comprise a composite of various materials or pieces of material, such as PTFE or other preferably biocompatible polymers or metals.

Referring to FIGS. 29A-R, an assembly and process for utilizing a tension prosthesis to generate compression along and adjacent the length of the tension prosthesis is depicted. A straight line embodiment is depicted, but similar technique may be utilized to generate compression along a curve to, for example, generate hoop stress or a "purse stringing" effect, as depicted in the mitral valve geometry modification embodiment of FIGS. 30A-M.

Figure 29E:
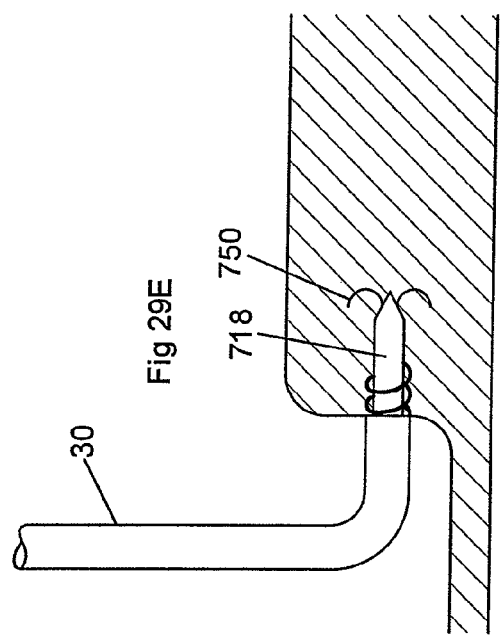
FIGS. 29A-R are schematic views of a sheath instrument, a needle instrument, a guide instrument, and a tension prosthesis deployed at a tissue mass according to one embodiment of the disclosed inventions.

Referring to FIG. 29A, a sheath instrument (30) is navigated to a targeted tissue mass (721). As shown in FIGS. 29B-C, a helical portion (748) may be utilized to engage the tissue mass, subsequent to which a needle instrument (718) may be forwarded into the subject tissue mass, as depicted in FIG. 29D. After the needle (718) is advanced forward, the position may be retained by deploying an anchoring mechanism (750), such as barbs, as depicted in FIG. 29E. With the needle instrument anchored in position, a guide instrument

Figure 29F:
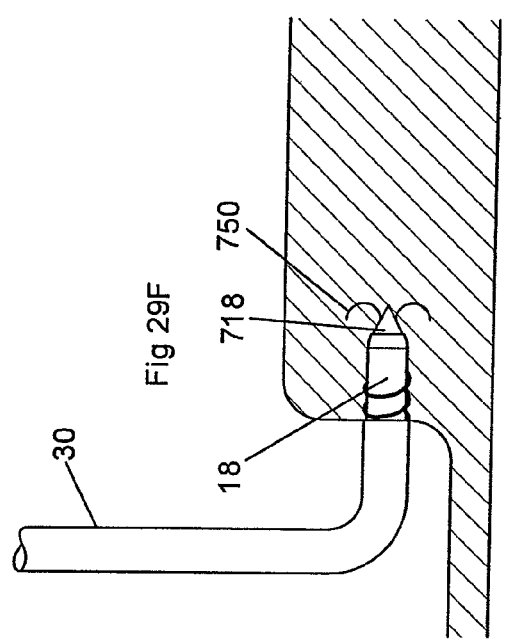
Figure 29G:
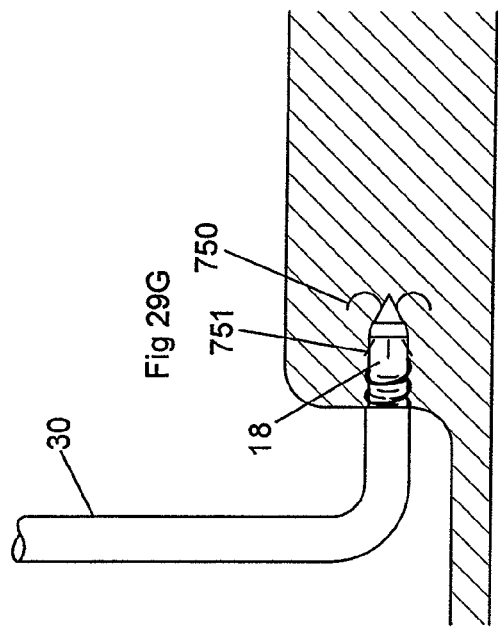
Figure 29H:
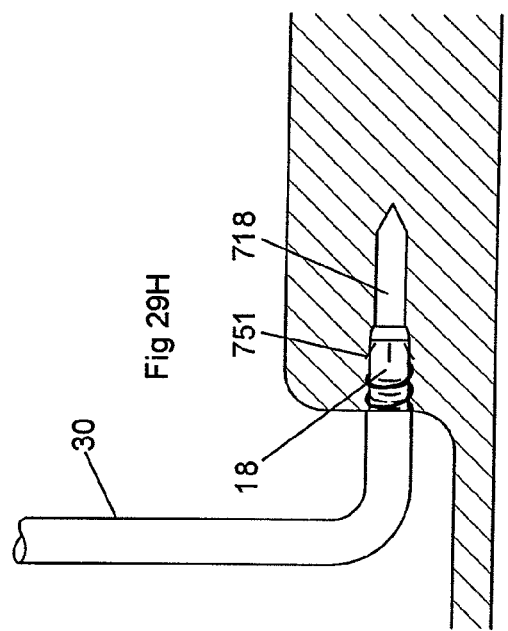

(18) may be forwarded, coaxially in this embodiment, over the needle instrument (718), as depicted in FIG. 29F. With the guide instrument advanced forward, the guide position may be retained by deploying an anchoring mechanism (751), such as barbs as depicted in FIG. 29G, while the needle instrument (718) is advanced yet forward, as depicted in FIG. 29H.

This subprocess of sequentially forwarding and anchoring the needle instrument (718) and guide instrument (18) may be repeated to incrementally move the guide/needle assembly forward through the tissue mass, as depicted in FIGS. 29I-N. Between or during incremental forwarding/anchoring moves, the trajectory of the assembly may be controllably modified as depicted in FIGS. 29K-L by utilizing the remote steerability of the robotic guide (18) instrument. Referring to FIGS. 29O-P, once the needle (718) and guide (18) instruments are advanced to a preferred distal position, a tension prosthesis (741) may be threaded through the guide instrument (18) and the distal anchor (742) of the tension prosthesis (741) may be expanded into place for form an anchor for the tension prosthesis. The tension prosthesis may be coupled, for example, to the distal end of the needle instrument or other elongate instrument suitable for deploying the prosthesis, and may be decoupled using a simple releasable mechanical linkage, electrolytically erodable linkage, male/female threaded interface, etc.

Referring to FIG. 29Q, with the tension prosthesis anchored, the guide instrument may be removed by pulling it proximally into the sheath instrument and out of the tissue mass. Finally, the tension prosthesis may be placed into tension with a proximally-applied load to place the adjacent tissue into compression (749) and/or shear stress, as depicted in FIG. 29R. A proximal anchor (not shown) may be utilized to lock the proximal end of the prosthesis into position and retain the tensile load.

Referring to FIGS. 30A-M, a tension prosthesis is utilized to create a hoop stress around the posterior aspect of a malformed mitral valve to modify the valve geometry and preferably decrease valve leakage by bringing the leaflets into better coaption. One of the problems commonly associated with mitral valve leakage is deformation of the posterior aspect of the mitral valve annulus away from the center of the heart (or away from the position of the tricuspid valve, for example).

Figure 30A:
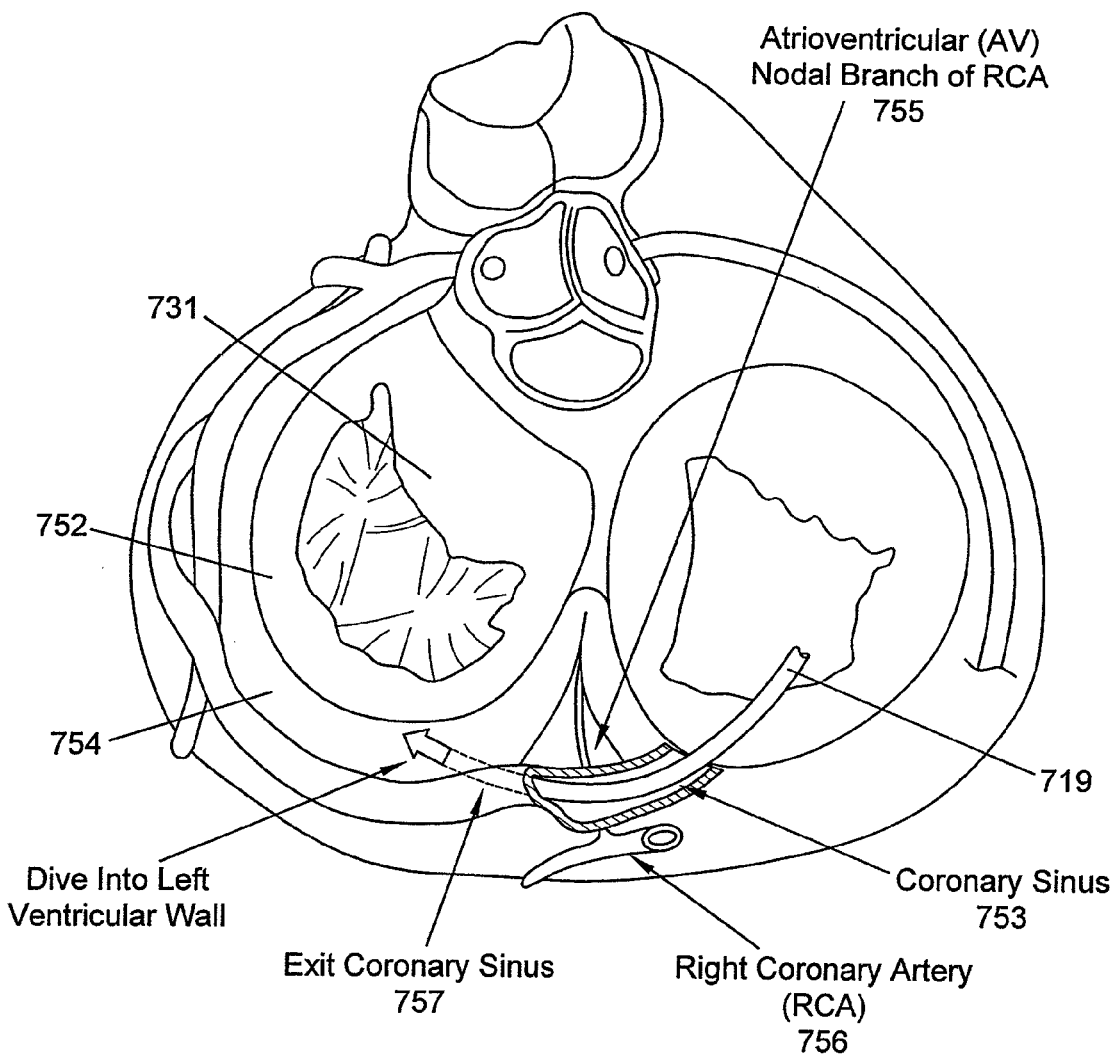
FIGS. 30A, 30C, 30J, 30L, and 30M are axial cross-sectional views of a heart being treated with an instrument assembly according to one embodiment of the disclosed inventions.
Figure 30B:
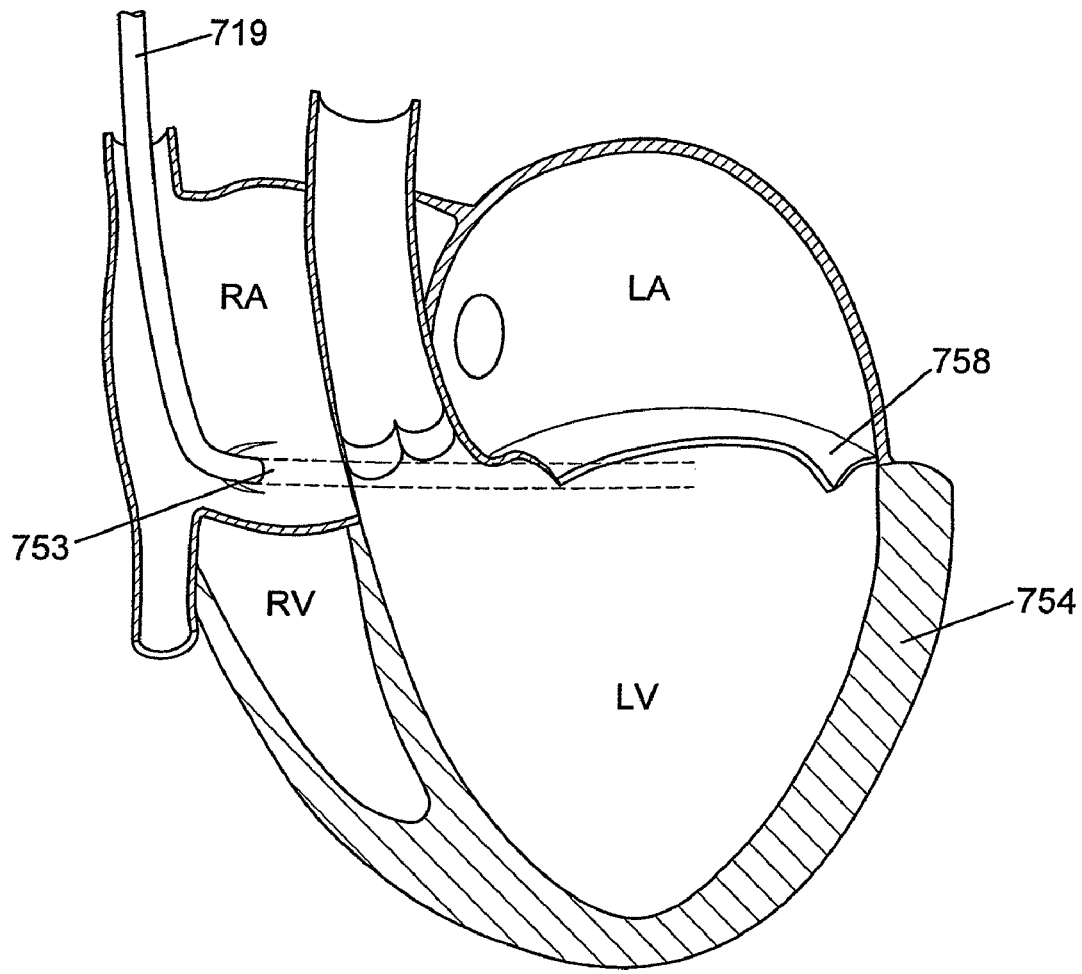
FIGS. 30B and 30K are longitudinal cross-sectional views of a heart being treated with an instrument assembly according to one embodiment of the disclosed inventions.

Referring to FIG. 30A, the coronary sinus is entered with a steerable guide/sheath instrument assembly from the inferior vena cava. After the instrument assembly (719) is advanced just past the position of the atrioventricular nodal branch (755) of the right coronary artery (756), a needle instrument is protruded out the distal end of the guide instrument and steered by the steerable guide instrument to exit the coronary sinus (753) and dive into the left ventricular wall myocardium (754). An anterior heart view of this pathway around the mitral valve annulus (758) is depicted in FIG. 30B.

Figure 30C:
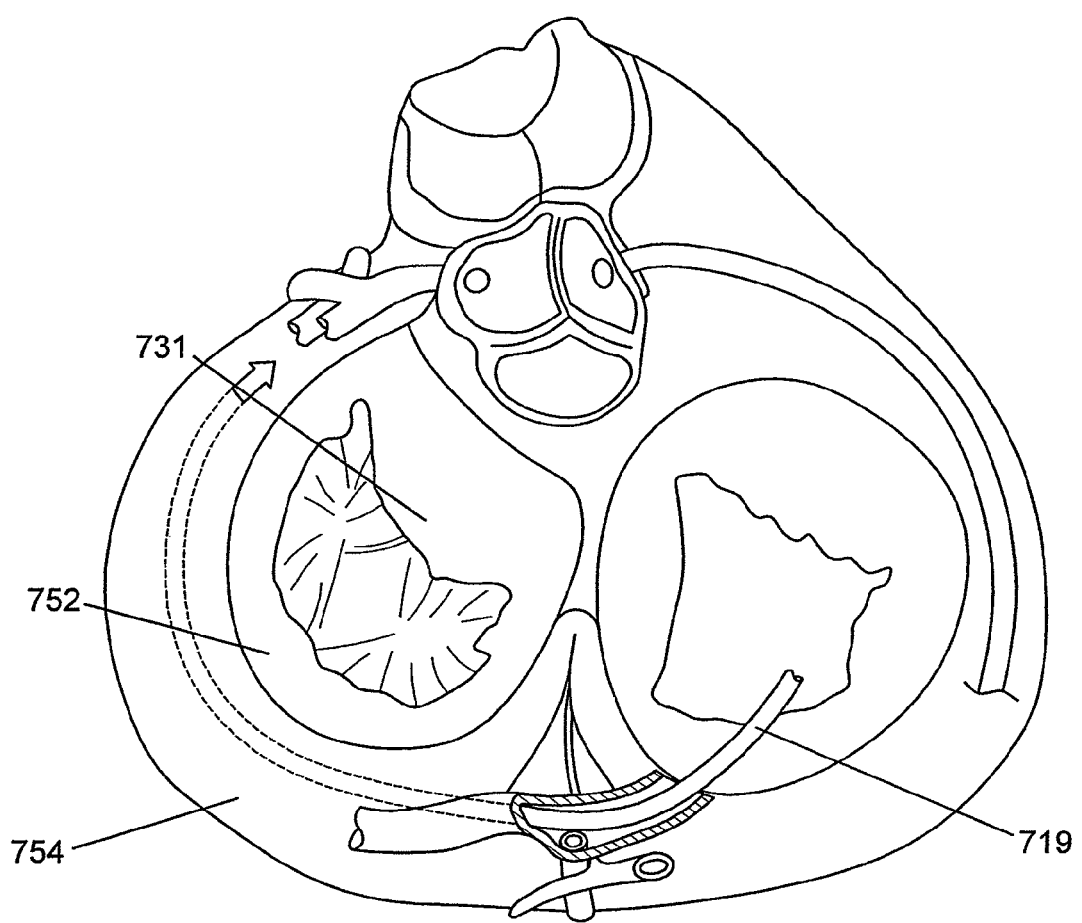
Figure 30D:
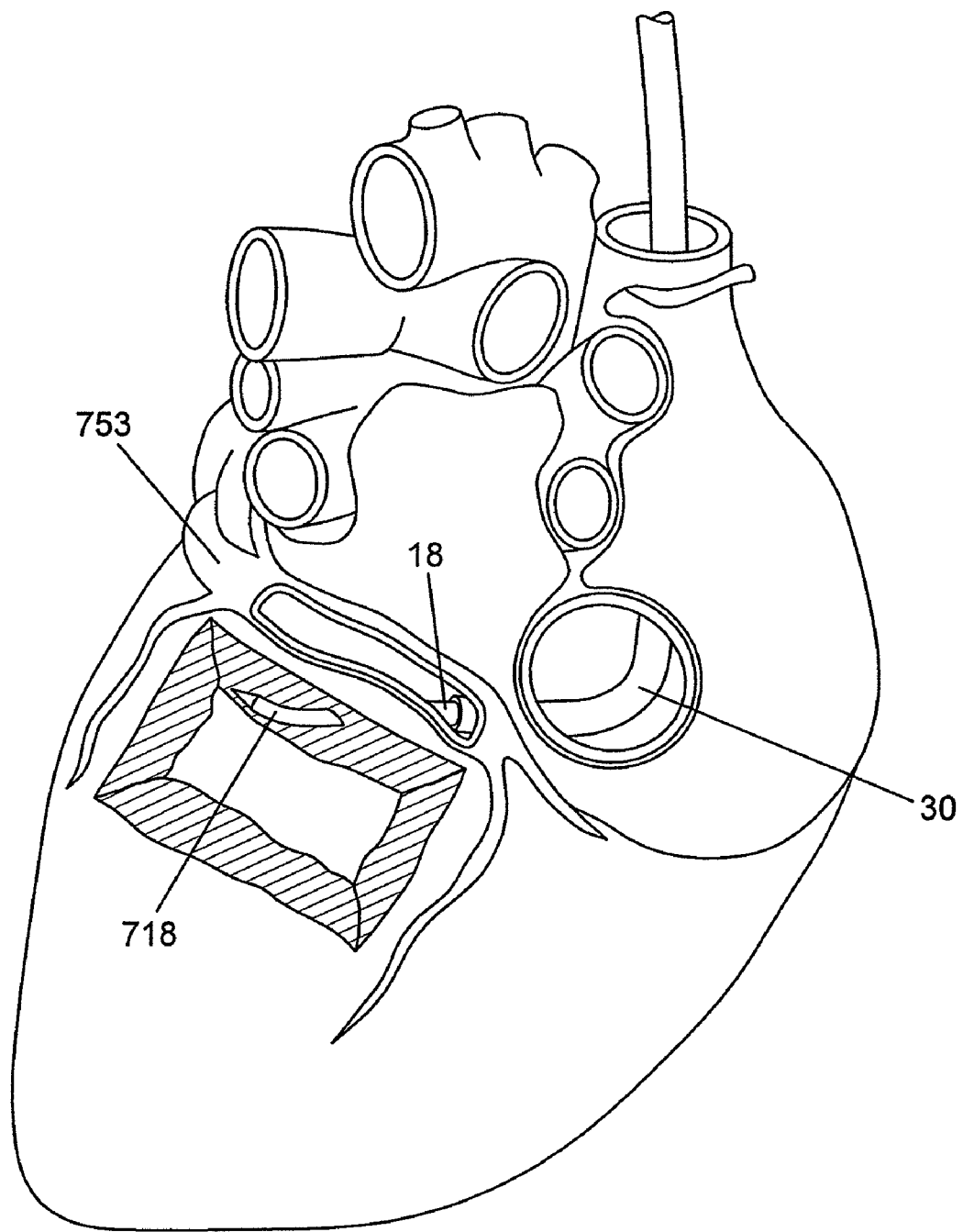
FIGS. 30D-I are perspective views of a heart being treated with an instrument assembly according to one embodiment of the disclosed inventions with portions of the coronary sinus and the left ventricular wall removed for clarity.
Figure 30E:
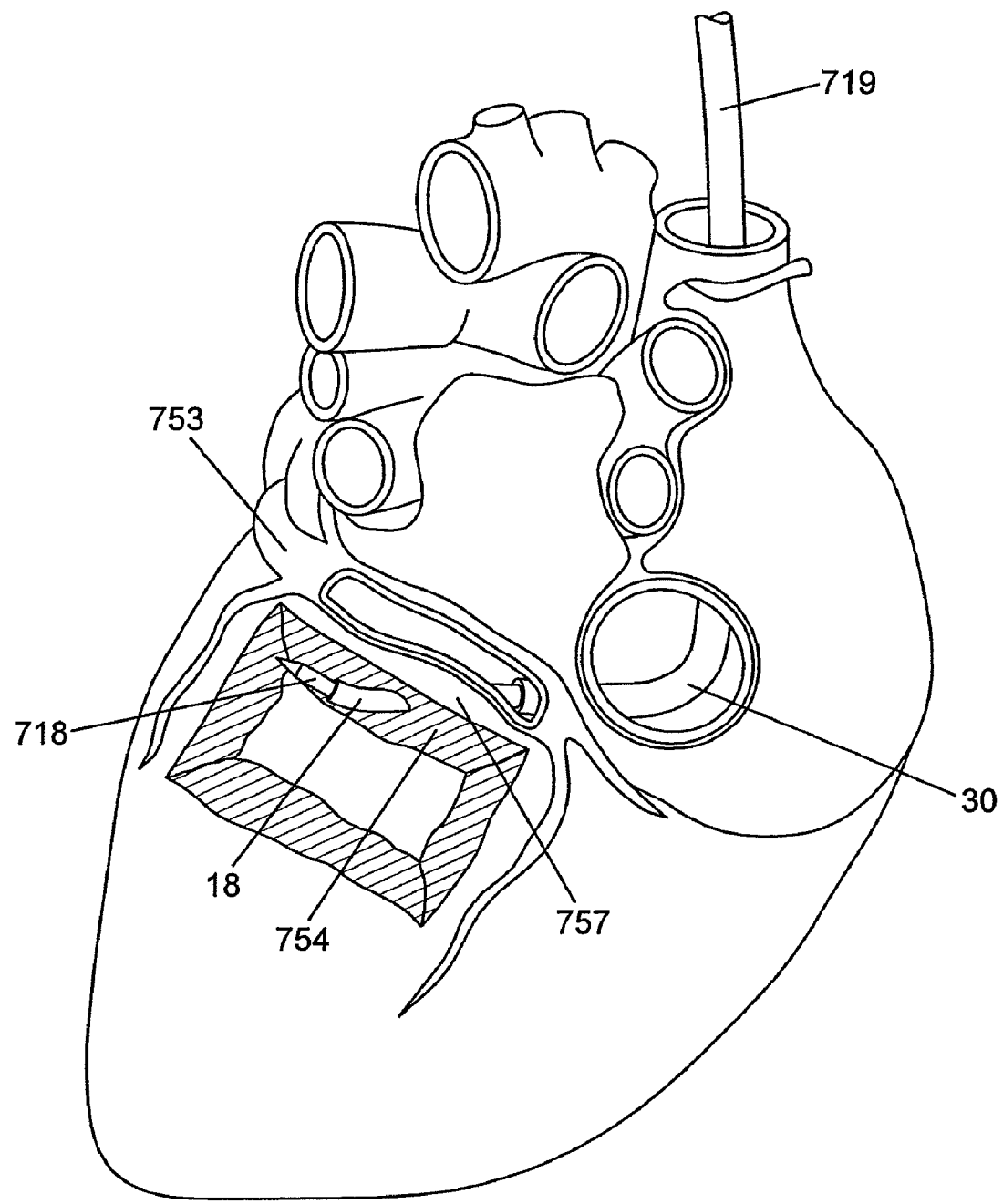
Figure 30F:
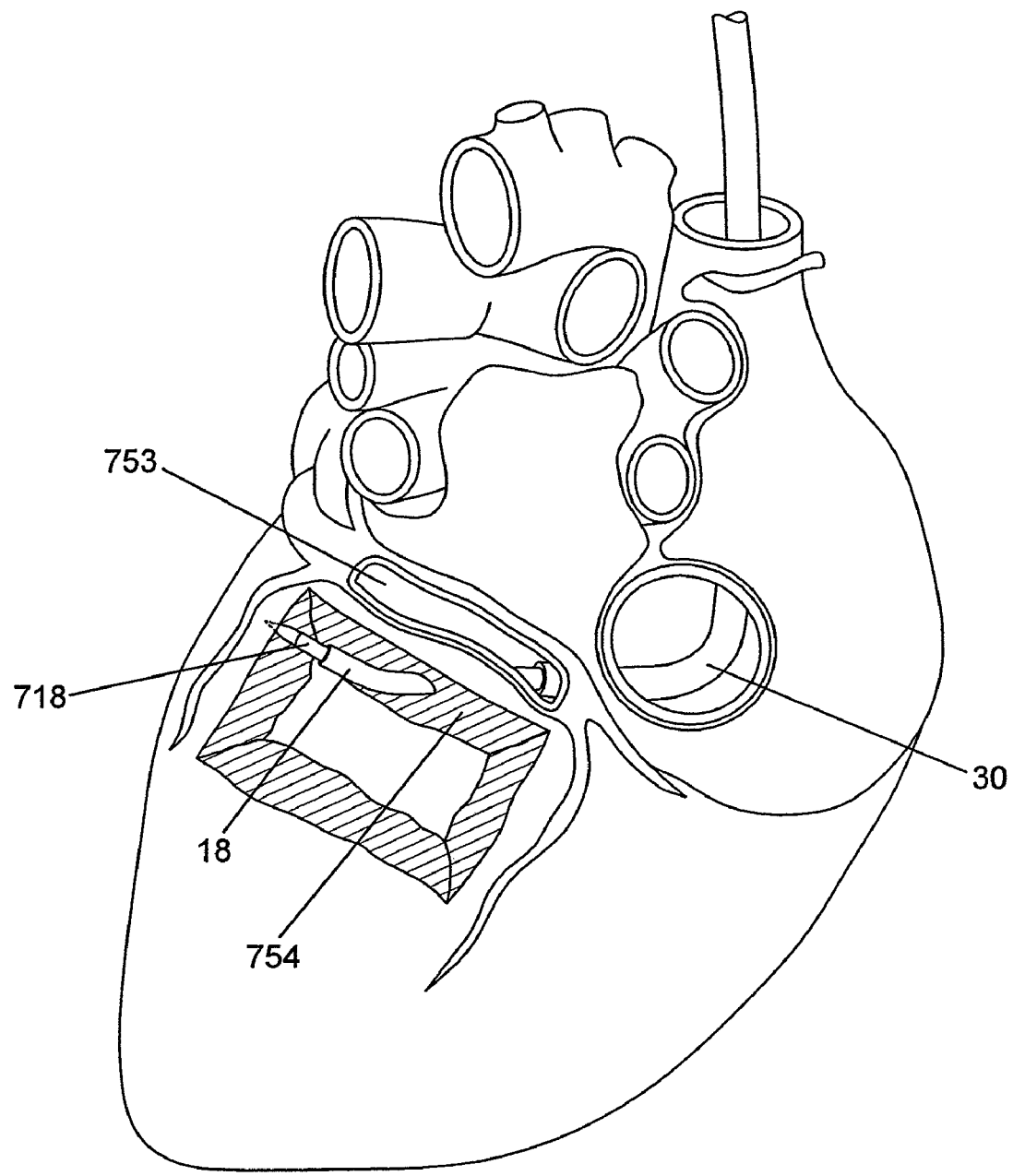
Figure 30G:
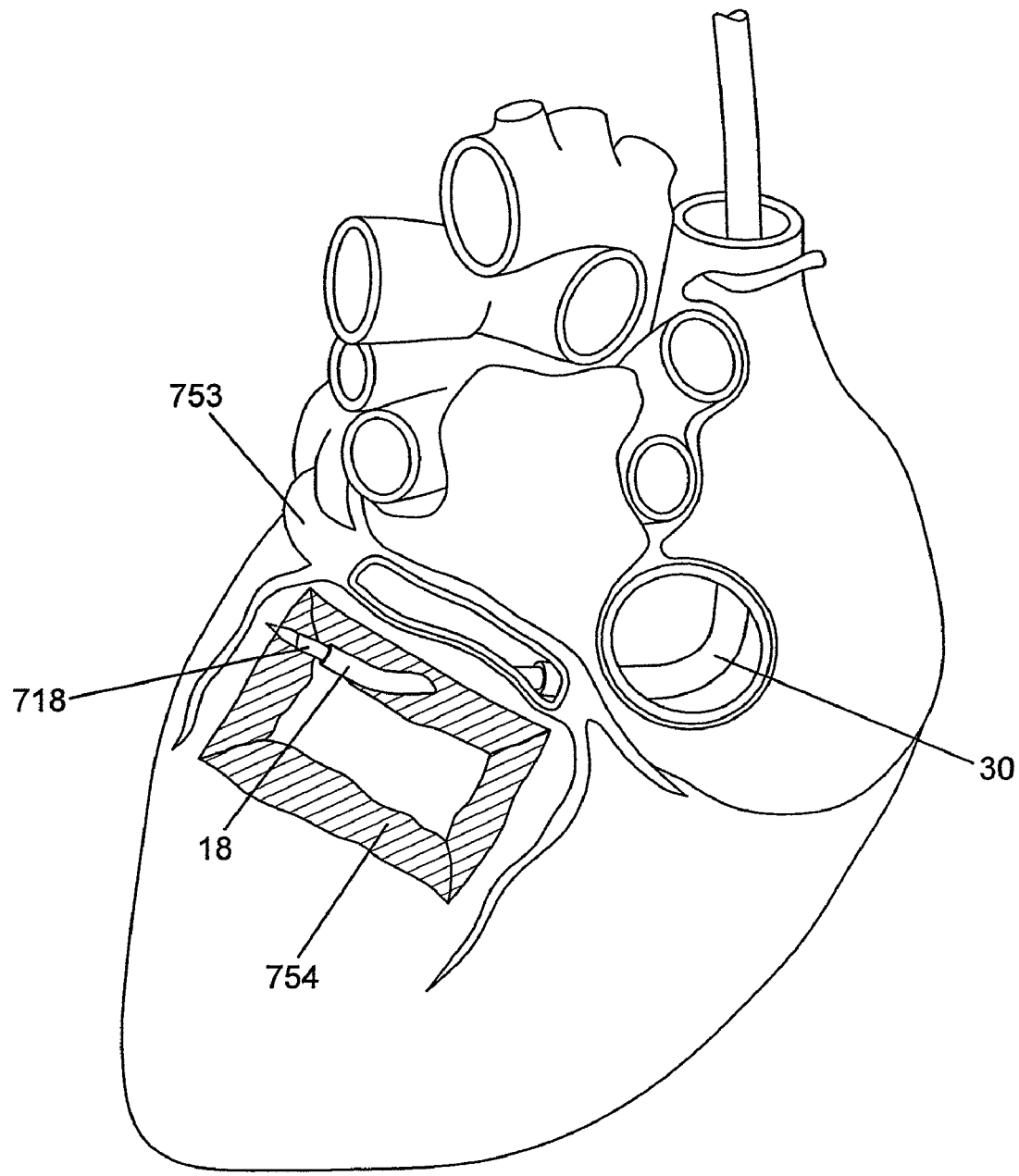
Figure 30H:
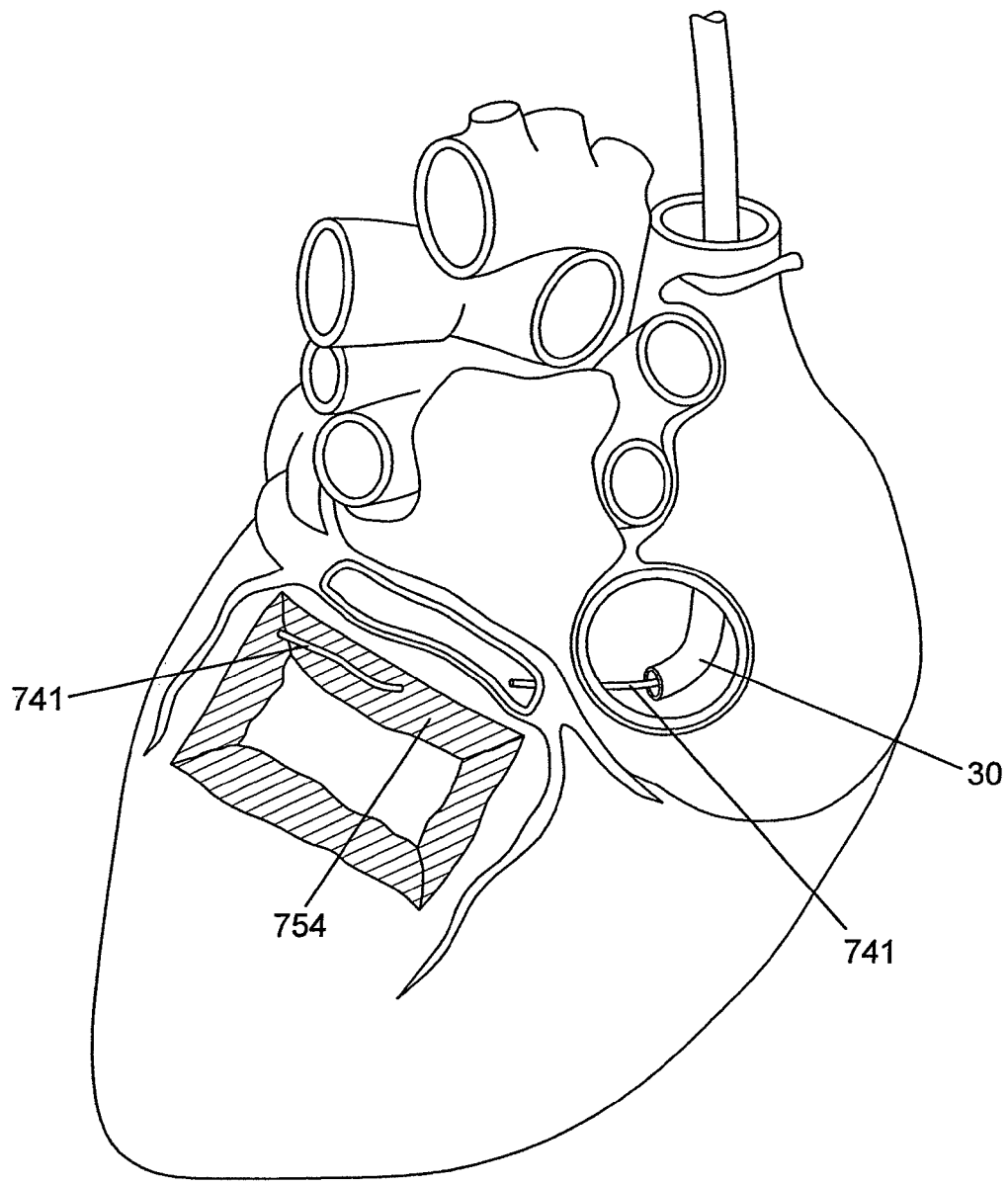
Figure 30I:
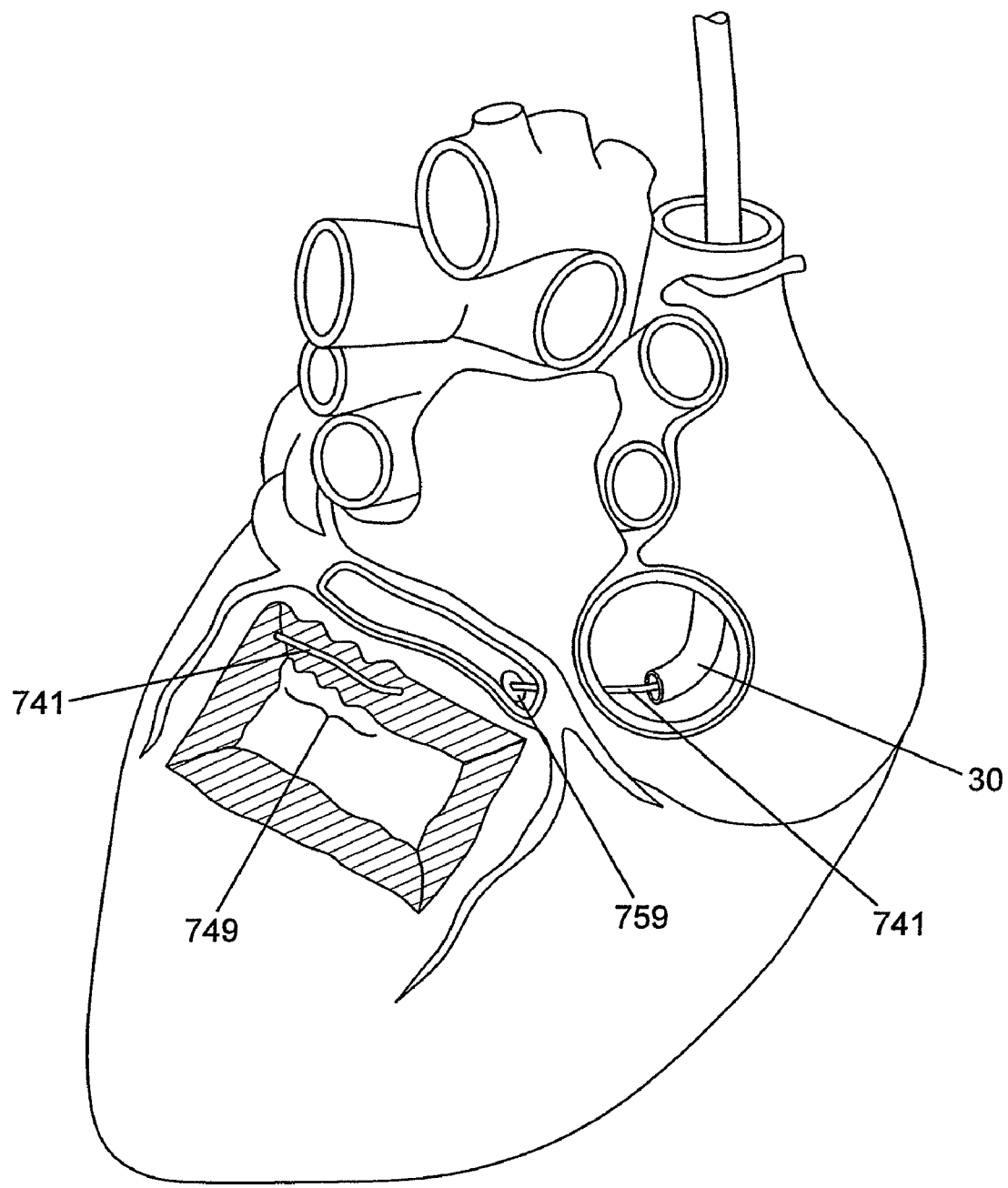

Referring to FIG. 30C, using the an incremental forwarding/anchoring/steering process such as that depicted in reference to FIGS. 29A-R, a tension prosthesis may be deployed in the wall of the myocardium (754) around the position of the posterior aspect (752) of the mitral valve (731) annulus. FIGS. 30D-G depict a needle/guide instrument assembly diving out of the coronary sinus and into/through the left ventricular wall (windows of the coronary sinus 753 and of the left ventricular wall 754 are removed for illustration purposes). FIG. 30H depicts a deployed tension prosthesis (741) after the needle and guide instruments and been pulled away proximally into the sheath instrument (30). FIG. 30I depicts hoop stress pushing portions of the left ventricular myocardium adjacent the posterior mitral valve annulus into circumferential compression (749), or "hoop stress", which is desired to pull the posterior mitral valve annulus into a more desirable shape.

Figure 30K:
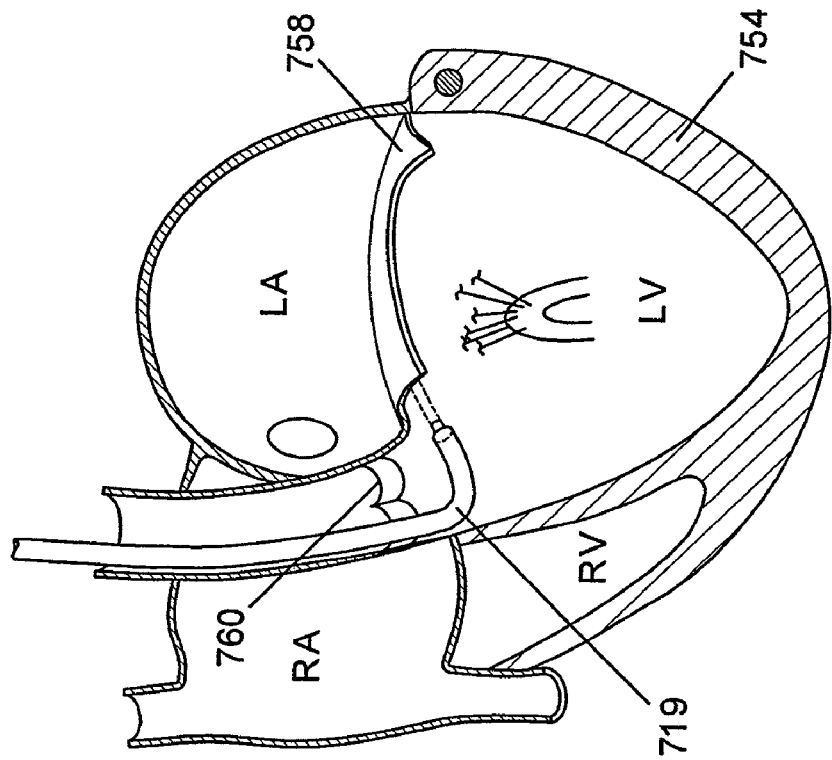
Figure 30J:
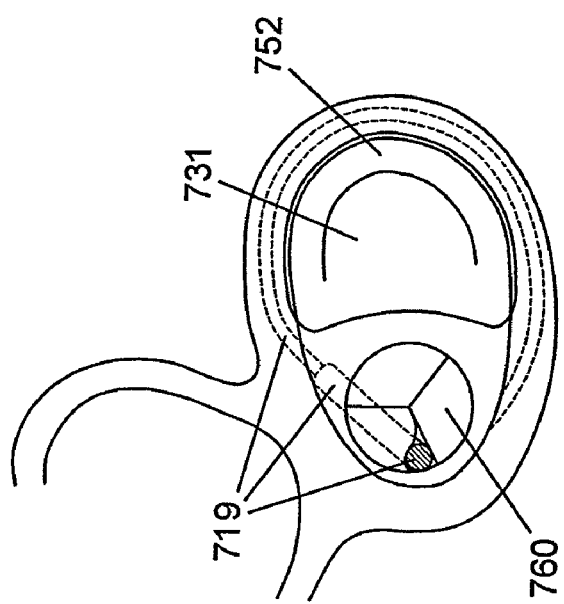
Figure 30M:
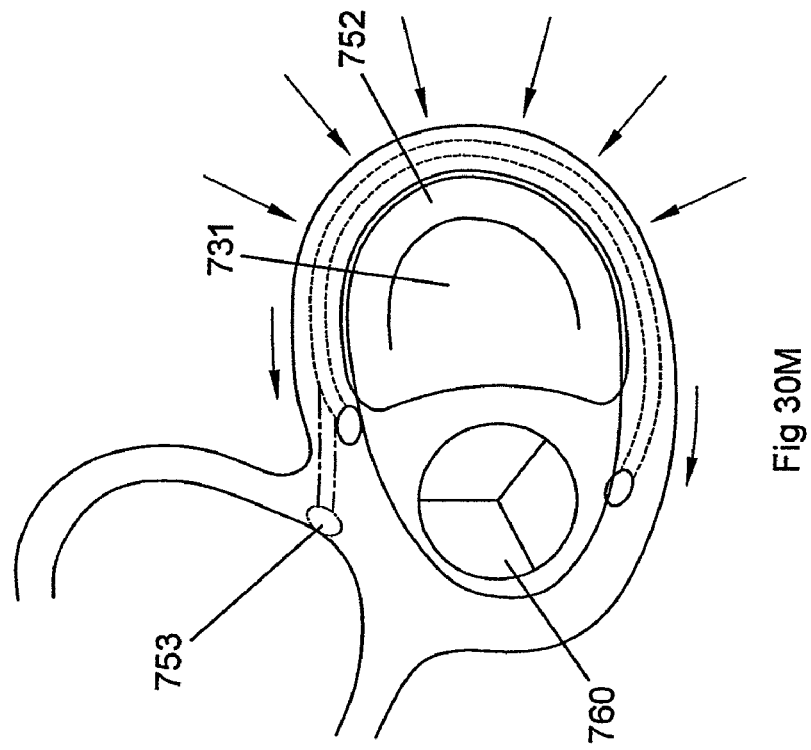
Figure 30L:
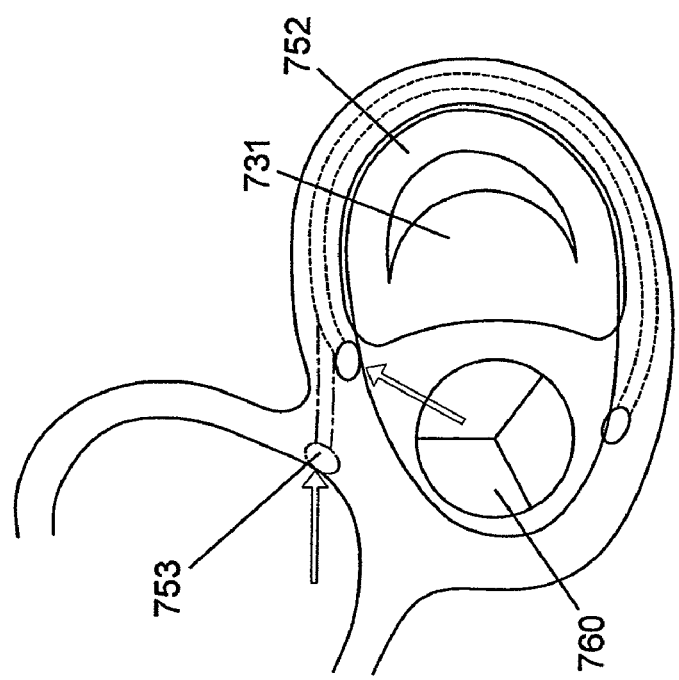

FIGS. 30J-K depict an embodiment wherein a similar result is achieved by navigating the instrument assembly (719) from a trans-aortic-valve (760) retrograde approach and diving into the left ventricular myocardium between the positions of the aortic (760) and mitral (731) valves. FIGS. 30L and 30M depict the preferred hoop stress geometric remodeling of the posterior mitral annulus (758)—both the trans-aortic-valve (760) retrograde and coronary sinus (753) approaches are depicted in dashed outlining.

Figure 31A:
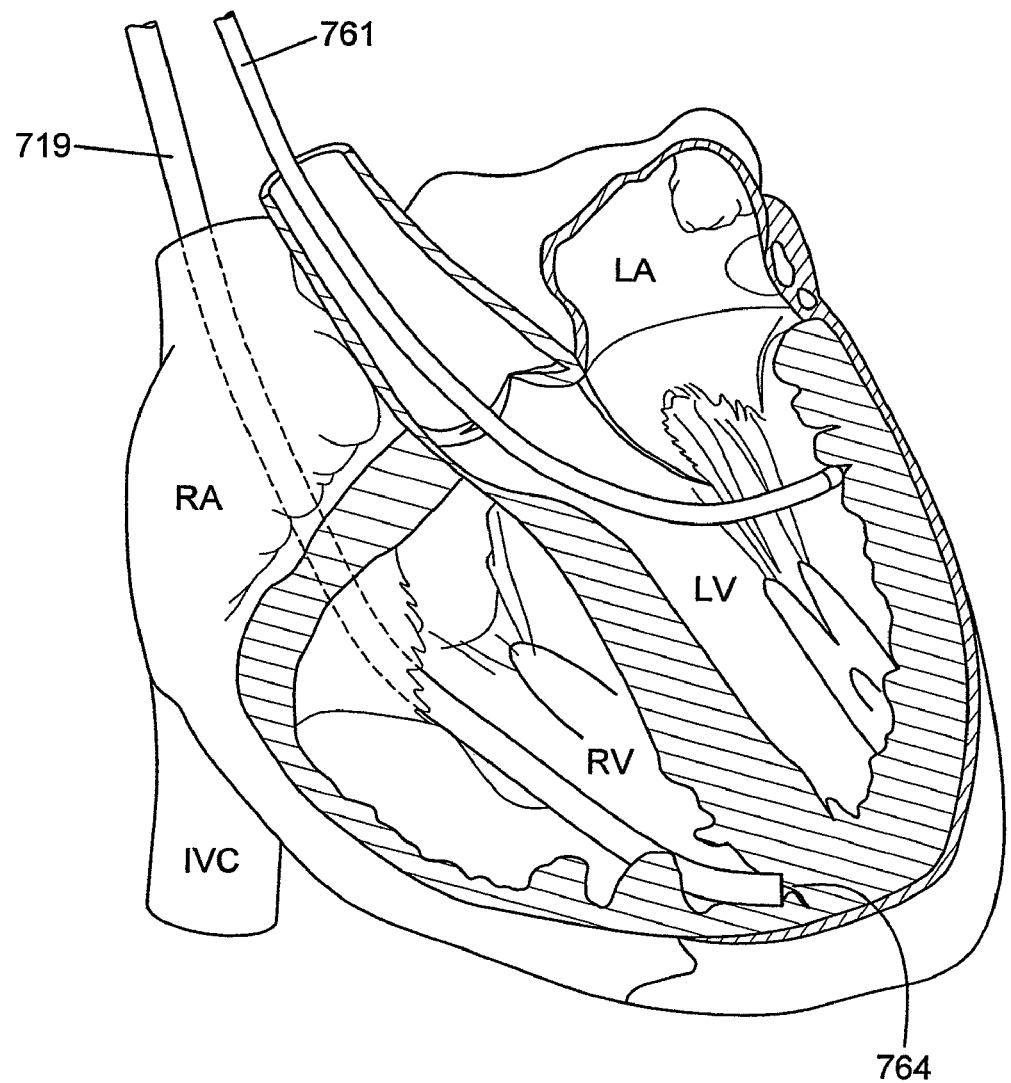
FIGS. 31A-D are perspective views of a heart being treated with an instrument assembly according to another embodiment of the disclosed inventions with portions of the left atrial wall and the left and right ventricular walls removed for clarity.
Figure 31B:
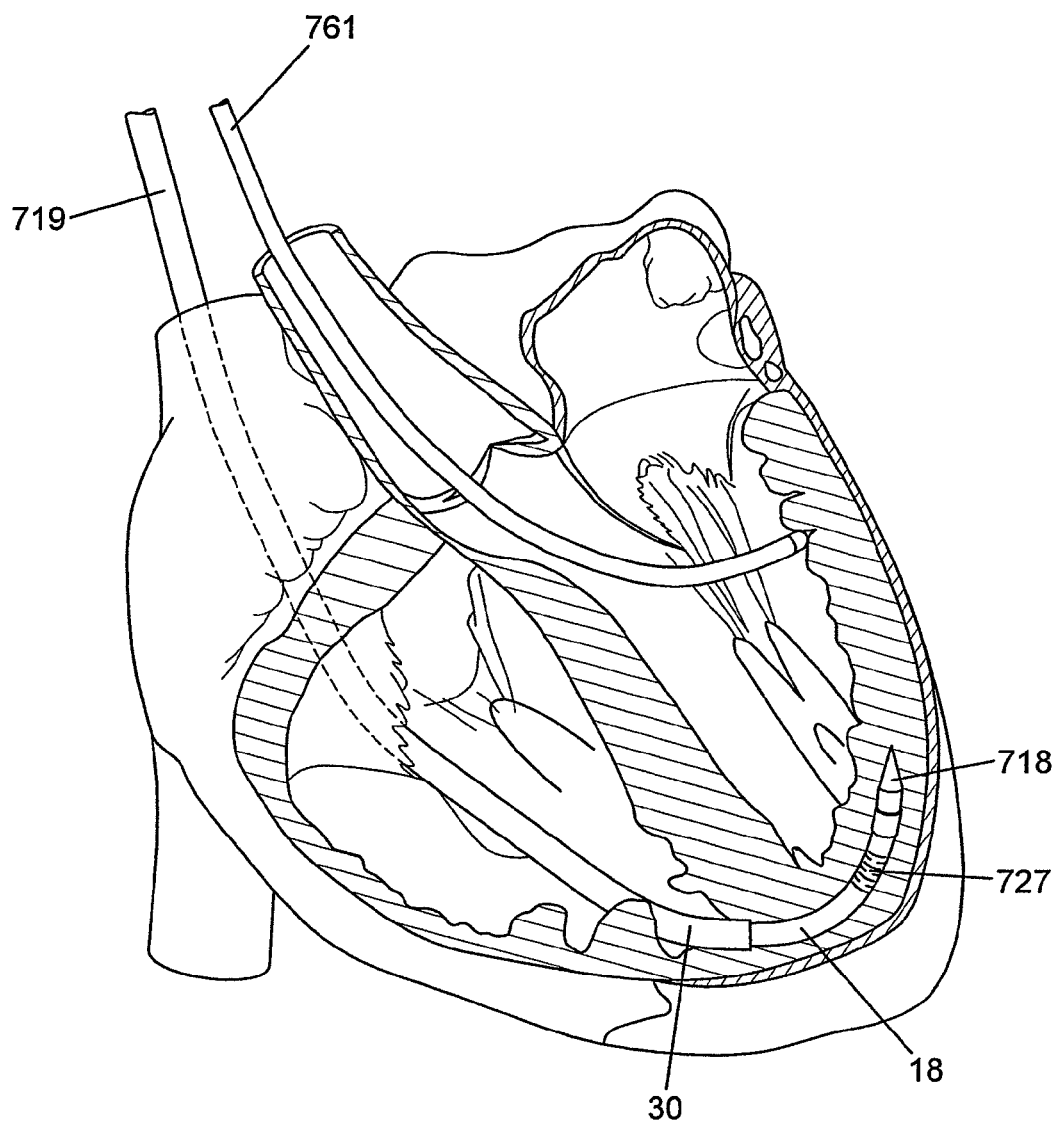
Figure 31C:
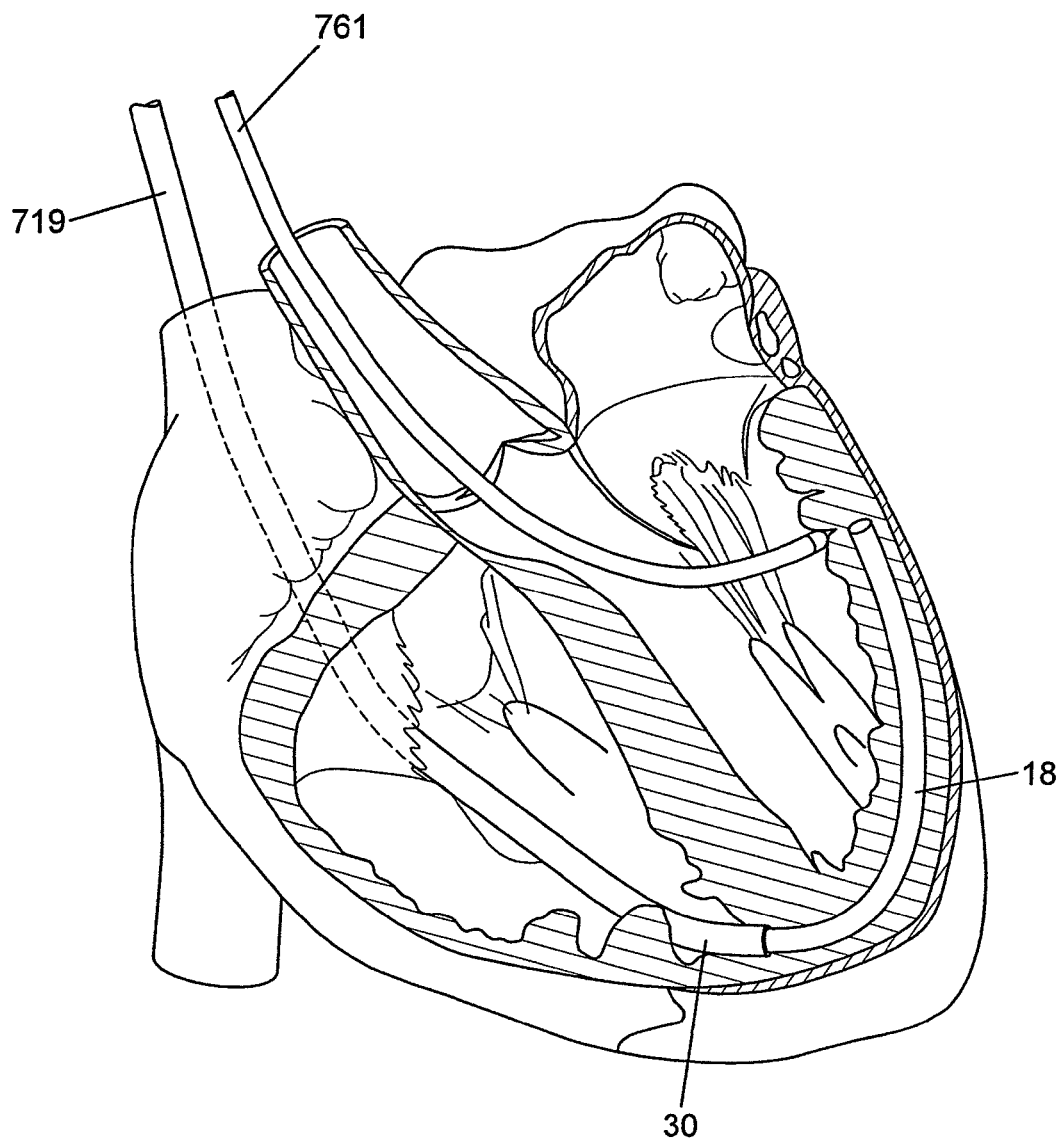
Figure 31D:
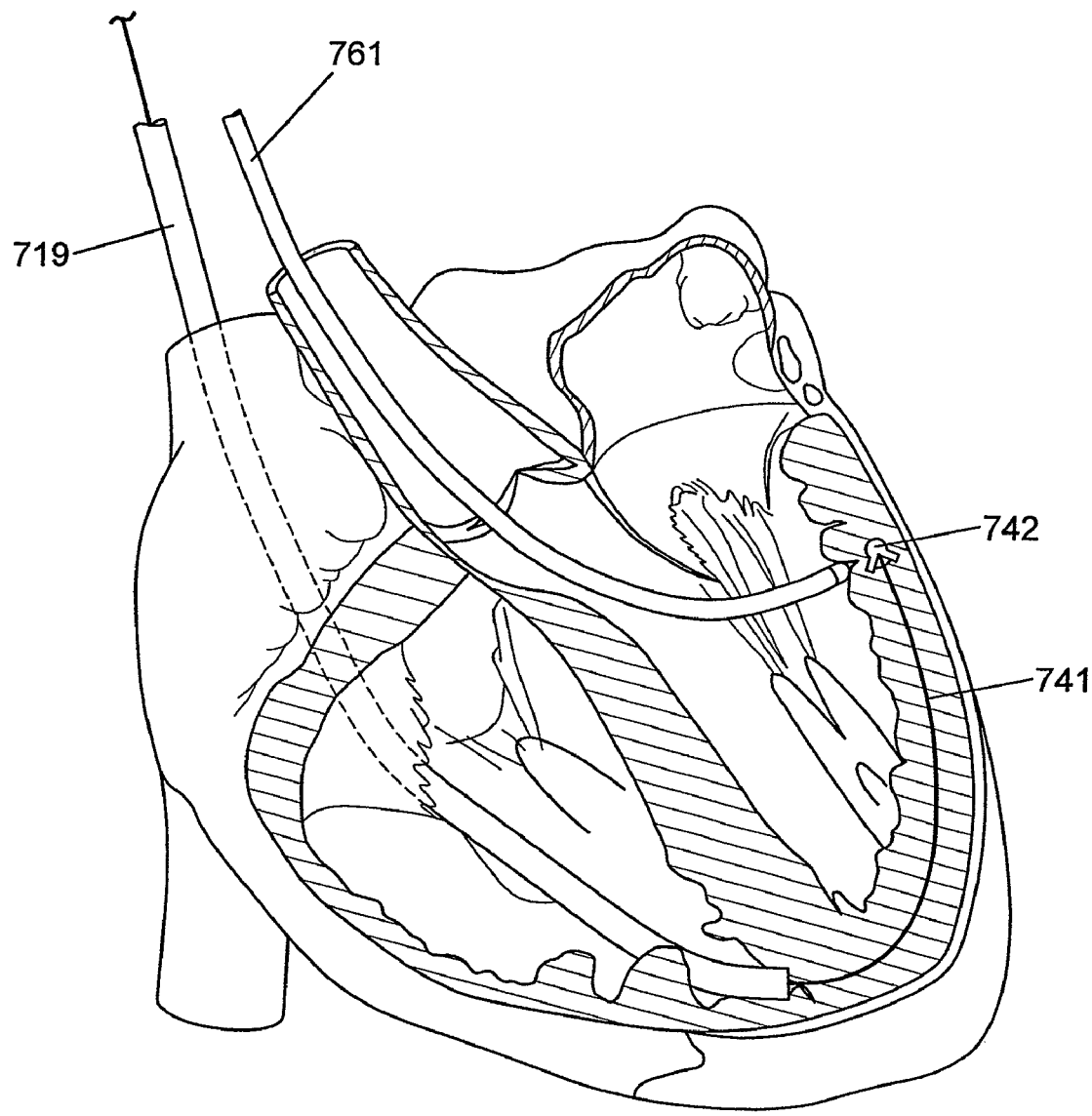

Referring to FIGS. 31A-D, placement of a tension prosthesis along the length of one aspect of the left ventricle is depicted. Such a tension prosthesis placement may be utilized to take up slack which may be the result of a myocardial infarction, congestive heart failure, etc. As shown in FIG. 31A, an assembly (719) comprising sheath, guide, and needle instruments may be navigated from the inferior vena cava, across the tricuspid valve, and toward the right ventricular apex (764). Referring to FIG. 31B, the needle instrument (718) and guide instrument (18) may then be deployed forward into the myocardium and steerably incrementally advanced using the aforementioned techniques. Referring to FIGS. 31C-D, upon arrival to a preferred target location in the myocardium, a tension prosthesis (741) may be deployed and the guide instrument (18) pulled away proximally.

Each of FIGS. 31A-D also depicts a second catheter instrument (761) placed trans-aortically into the left ventricle. This second catheter instrument may be utilized to monitor the position of needle/guide instrument assembly (719) within the ventricular wall utilizing ultrasound, localization (magnetic, conduction based, voltage based, etc), and other techniques to increase safety and precision of the deployment of the tension prosthesis. Similarly, a second instrument may be utilized, for example, in the circumflex artery and/or coronary sinus to carefully monitor the position of adjacent tissue structures and incrementally moving instruments in procedures such as those depicted in FIGS. 30A-30M.

While multiple embodiments and variations of the many aspects of the invention have been disclosed and described herein, such disclosure is provided for purposes of illustration only. For example, depending upon the medical application, it may be desirable to have a guide instrument with less than four control elements, combined with a sheath instrument, or perhaps combined with a pre-bent, unsteerable sheath, or perhaps with no sheath at all. The instrument driver may be tailored to match the instrument configuration, with less motors and gearboxes for less control elements, or variation in the configuration for actuating a given control element interface assembly, and associated variation in the tensioning mechanism and number of control element pulleys associated with the pertinent control element interface assembly (one pulley and one cable per control element interface assembly, two pulleys and two cables per control element interface assembly, slotted, split carriage, and winged split carriage embodiments, various tensioning embodiments, etc).

What is claimed:
1. A robotic catheter system, comprising:
a controller including a master input device, an instrument driver in communication with the controller, an elongate flexible guide instrument operatively coupled to the instrument driver, an elongate flexible member extending through a lumen of the guide instrument, the system characterized in that it further comprises:

a fluid injection needle carried by a distal portion of the flexible member, wherein the needle may be advanced from, or retracted into, a side of the flexible member; and an imaging device carried by the flexible member to provide a side-oriented field of view configured to capture images of at least a portion of the needle as it is advanced from the side of the flexible member.

2. The system of claim 1, the fluid injection needle comprising an internal lumen in fluid communication with a fluid source, and having one or more injection ports in communication with the internal lumen.

3. The system of claim 1, comprising a plurality of fluid injection needles carried on a distal end portion of the flexible member.

4. The system of claim 1, further comprising a helical anchor member that may be rotatably advanced from, and retracted into, a distal end portion of the guide instrument.

5. The system of claim 1, further comprising one or more lateral anchor members that may be deployed from a side of the fluid injection needle.

6. The system of claim 1, further comprising one or more anchor members that may be deployed from a side of the guide instrument.

7. The system of claim 1, further comprising a source of RF energy selectively electrically coupled to the fluid injection needle, whereby RF energy may be delivered to tissue proximate the needle.

8. The system of claim 1, further comprising a mechanical lever configured for actuating advancement and retraction of the fluid injection needle.

9. The system of claim 1, wherein the imaging device comprises one of an ultrasound array, CCD device, and an optical camera.

10. The system of claim 1, wherein the fluid injection needle comprises an electrode.

* * * * *